United States Patent
Rössle et al.

(10) Patent No.: US 9,938,305 B2
(45) Date of Patent: Apr. 10, 2018

(54) AMINOSILYL-SUBSTITUTED DIARYLETHENE COMPOUNDS FOR ANIONIC POLYMERISATION

(71) Applicant: Trinseo Europe GmbH, Horgen (CH)

(72) Inventors: Michael Rössle, Schkopau (DE); Christian Döring, Schkopau (DE); Sven Thiele, Halle (DE); Daniel Heidenreich, Schkopau (DE); Nadine Schübel, Schkopau (DE); Christiane Jacobi, Schkopau (DE)

(73) Assignee: TRINSEO EUROPE GMBH, Horgen (CH)

( * ) Notice: Subject to any disclaimer, the term of this patent is extended or adjusted under 35 U.S.C. 154(b) by 0 days.

(21) Appl. No.: 15/326,832

(22) PCT Filed: Jul. 14, 2014

(86) PCT No.: PCT/EP2014/065027
§ 371 (c)(1),
(2) Date: Jan. 17, 2017

(87) PCT Pub. No.: WO2016/008507
PCT Pub. Date: Jan. 21, 2016

(65) Prior Publication Data
US 2017/0204119 A1     Jul. 20, 2017

(51) Int. Cl.
| C07F 7/10 | (2006.01) |
| C08K 5/01 | (2006.01) |
| C07F 7/12 | (2006.01) |
| C07F 7/14 | (2006.01) |
| C08F 236/10 | (2006.01) |
| C08J 3/24 | (2006.01) |
| C07F 7/08 | (2006.01) |
| C08F 4/48 | (2006.01) |

(52) U.S. Cl.
CPC ............. *C07F 7/10* (2013.01); *C07F 7/0849* (2013.01); *C07F 7/0863* (2013.01); *C07F 7/0879* (2013.01); *C07F 7/12* (2013.01); *C07F 7/14* (2013.01); *C08F 236/10* (2013.01); *C08J 3/24* (2013.01); *C08K 5/01* (2013.01); *C08J 2309/06* (2013.01)

(58) Field of Classification Search
CPC .......... C07F 7/0849; C07F 7/10; C08F 4/463; C08F 4/48; C08F 236/10
USPC ........................... 526/178; 556/410; 525/342
See application file for complete search history.

(56) References Cited

U.S. PATENT DOCUMENTS

| 3,078,254 A | 2/1963 | Zelinski et al. |
| 3,244,664 A | 4/1966 | Zelinski et al. |
| 3,281,383 A | 10/1966 | Zelinski et al. |
| 3,629,213 A | 12/1971 | Onishi et al. |
| 3,692,874 A | 9/1972 | Farrar et al. |
| 3,951,936 A | 4/1976 | Hanlon |
| 3,978,103 A | 8/1976 | Meyer-Simon et al. |
| 4,048,206 A | 9/1977 | Voronkov et al. |
| 4,474,908 A | 10/1984 | Wagner |
| 4,616,069 A | 10/1986 | Watanabe et al. |
| 4,689,368 A | 8/1987 | Jenkins |

(Continued)

FOREIGN PATENT DOCUMENTS

| EP | 0 924 214 | 11/1998 |
| EP | 0 964 008 | 6/1999 |

(Continued)

OTHER PUBLICATIONS

"Rubber Compounding", *Kirk-Othmer Encyclopedia of Chemical Technology* 3rd, Ed., (Wiley Interscience, N.Y. 1982), vol. 20, 60 pages.

(Continued)

*Primary Examiner* — Fred M Teskin
(74) *Attorney, Agent, or Firm* — Eric D. Babych; Brinks Gilson & Lione

(57) ABSTRACT

The invention related to novel compounds useful as modifying monomers and precursors for polymerization initiators. The invention further relates to a method of making the polymerization initiators and resulting polymers. The invention also relates to polymer compositions comprising the polymer of the invention and further components such as extender oils, fillers, vulcanizing agents etc., and to corresponding vulcanized polymer compositions and articles comprising vulcanized parts made from the vulcanized polymer composition.

Formula 1

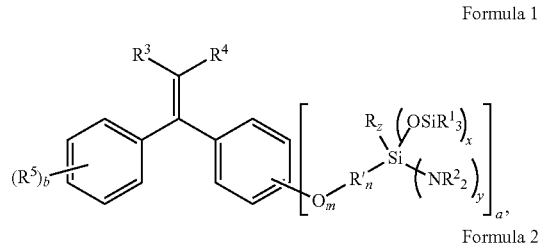

Formula 2

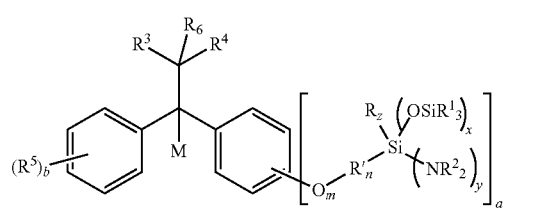

29 Claims, No Drawings

(56) References Cited

U.S. PATENT DOCUMENTS

| | | | |
|---|---|---|---|
| 4,931,376 A | | 6/1990 | Ikematsu et al. |
| 5,081,191 A | * | 1/1992 | Quirk .................... C08F 297/02 |
| | | | 525/288 |
| 5,086,136 A | | 2/1992 | Takashima et al. |
| 5,089,574 A | | 2/1992 | Castner |
| 5,134,199 A | | 7/1992 | Hattori et al. |
| 5,448,002 A | | 9/1995 | Castner |
| 5,753,579 A | | 5/1998 | Jalics et al. |
| 5,753,761 A | | 5/1998 | Sandstrom et al. |
| 5,834,573 A | | 11/1998 | Castner |
| 6,018,007 A | | 1/2000 | Lynch |
| 6,103,842 A | | 8/2000 | Halasa et al. |
| 6,184,168 B1 | | 2/2001 | Lynch |
| 6,229,036 B1 | | 5/2001 | Batz-Sohn et al. |
| 6,310,152 B1 | | 10/2001 | Castner |
| 6,489,415 B2 | | 12/2002 | Hsu et al. |
| 6,627,715 B2 | | 9/2003 | Halasa et al. |
| 6,693,160 B1 | | 2/2004 | Halasa et al. |
| 6,777,569 B1 | | 8/2004 | Westmeyer et al. |
| 6,818,710 B2 | * | 11/2004 | Oshima ..................... C08F 8/32 |
| | | | 525/272 |
| 7,868,081 B2 | | 1/2011 | Mori et al. |
| 8,030,406 B2 | | 10/2011 | Mori et al. |
| 2003/0065114 A1 | | 4/2003 | Castner |
| 2003/0114592 A1 | | 6/2003 | Brockmann et al. |
| 2003/0114611 A1 | | 6/2003 | Brockmann et al. |
| 2005/0124740 A1 | | 6/2005 | Klockmann et al. |
| 2005/0159513 A1 | | 7/2005 | Henning et al. |
| 2013/0131263 A1 | | 5/2013 | Nebhani et al. |

FOREIGN PATENT DOCUMENTS

| | | |
|---|---|---|
| EP | 1 367 069 | 12/2003 |
| EP | 2 085 419 | 8/2009 |
| JP | H11-301794 A | 11/1999 |
| JP | 2011-074310 A | 4/2011 |
| JP | 2012-167207 A | 9/2012 |
| JP | 2012-241112 A | 12/2012 |
| JP | 2013-159770 A | 8/2013 |
| JP | 2013-163761 A | 8/2013 |
| JP | 2013-249418 A | 12/2013 |
| WO | WO 2000/050478 | 8/2000 |
| WO | WO 2000/050479 | 8/2000 |
| WO | WO 2007/047943 | 4/2007 |
| WO | WO 2009/148932 | 12/2009 |
| WO | WO 2011/002830 A2 | 1/2011 |
| WO | WO 2014/040639 | 3/2014 |
| WO | WO 2014/040640 | 3/2014 |

OTHER PUBLICATIONS

"Rubber, Vulcanized or Thermoplastic-Determination of Dynamic Properties—Part 1: General Guidance" *International Organization for Standardization*, 4664-1:2005, Feb. 15, 2005, 30 pages.

Aoki et al., *Tetrahedron: Asymmetry*, vol. 15, 2004, pp. 1771-1777.

Blümke et al., *Organic Letters*, vol. 13, No. 24, 2011, pp. 6440-6443.

Caron et al., *Pract. Synth. Org. Chem.*, 2011, pp. 279-340.

Corriu et al., *J. Chem. Soc., Chem. Commun.*, 1972 pp. 144a.

Del Valle et al., *J. Org. Chem.*, vol. 55, 1990, pp. 3019-3023.

Denmark et al., *J. Am. Chem. Soc.*, vol. 130, 2008, pp. 16382-16393.

Gomes et al., *Organic Letters*, vol. 5, No. 7, 2003, pp. 1043-1045.

Hirao et al., *Prog. Polym. Sci.*, vol. 30, 2005, pp. 111-125.

Hirao et al., *Progress in Polymer Science*, vol. 30, 2005, pp. 111-182.

Ikegami et al., *J. Org. Chem.*, vol. 68, 2003), pp. 2195-2199.

Kim et al., *Functional Polymers*, Chapter 7, 1998, pp. 85-95.

King et al., *J. Chem. Soc., Chem. Commun.*, 1977, pp. 683-684.

Krasovskiy et al., *Synthesis*, 2006, pp. 890-891.

Kubo et al., *Macromolecules* vol. 36, 2003, pp. 9264-9266.

Li et al., *J. Org. Chem.*, vol. 70, 2005, pp. 2832-2834.

Manolikakes et al., *J. Org. Chem.*, vol. 73, 2008, pp. 8422-8436.

Manolikakes, G. et al., "Negishi Cross-Couplings of Unsaturated Halides Bearing Relatively Acidic Hydrogen Atoms with Organozinc Reagents", *Ludwig-Maximilians-Universität München, Department Chemie*, 2008, 137 pages.

Mee et al., *Angew. Chem. Int. Ed.*, vol. 43, 2004, pp. 1132-1136.

Negishi et al., *J. Am. Chem. Soc.*, vol. 102, No. 9, 1980 pp. 3298-3299.

Negishi et al., *J. Org. Chem.*, vol. 42, No. 10, 1977, pp. 1821-1823.

Seechurn et al., *Angew. Chem. Int Ed.*, vol. 51, 2012, pp. 5062-5085.

Sekine et al., *Organic Letters*, vol. 15, No. 3, 2013, pp. 714-717.

Starflinger et al., *J. Org. Chem.*, vol. 51, 1986, pp. 37-40.

Stille, *Angew. Chem., Int. Ed. Engl.*, vol. 25, 1986, pp. 508-524.

Taber et al., *J. Org. Chem.*, vol. 78, 2013, pp. 9772-9780.

Tamao et al., *J. Am. Chem. Soc.*, vol. 94, No. 12, 1972, pp. 4374-4376.

Tamao et al., *Tetrahedron*, vol. 44, No. 13, 1988, pp. 3997-4007.

Tanaka et al., *Polymer*, vol. 22, 1981 pp. 1721-1723.

van Walree et al., *Eur. J. Org. Chem.*, 2004, pp. 3046-3056.

Yin et al., *Applied Organometallic Chemistry*, vol. 27, 2013, pp. 85-88.

* cited by examiner

AMINOSILYL-SUBSTITUTED DIARYLETHENE COMPOUNDS FOR ANIONIC POLYMERISATION

This application claims priority to International Application No. PCT/EP2014/065027 filed Jul. 14, 2014; the entire contents of which is incorporated herein by reference.

FIELD OF THE INVENTION

This invention relates to novel aminosilyl-substituted diarylethene compounds which may be used both as modifying monomers in an anionic polymerization, as chain end modifiers and as precursors for polymerization initiators for use in the anionic polymerization. The invention also relates to polymers, including modified (chain end- or backbone-modified) polymers, prepared with the novel compounds, as modifying monomers and/or initiator precursors, and to polymer compositions made therefrom. The invention furthermore relates to the use of these compositions in the preparation of vulcanized compositions and articles prepared from the same. The polymer compositions are useful in the preparation of vulcanized and, thus, cross-linked elastomeric compositions having relatively low hysteresis loss, good grip properties and high abrasion resistance. Such compositions are useful in many articles, including tire treads having low heat build-up, low rolling resistance and high abrasion resistance, in combination with a good balance of other desirable physical and chemical properties, for example, good wet grip, ice grip and tensile strength and excellent processability.

BACKGROUND OF THE INVENTION

Increasing oil prices and national legislation requiring the reduction of automotive carbon dioxide emissions force tire and rubber producers to produce "fuel-efficient" and thus fuel-saving tires. One general approach to obtain fuel-efficient tires is to produce tire formulations which have reduced hysteresis loss. A major source of hysteresis in vulcanized elastomeric polymers is attributed to free polymer chain ends, i.e. the section of the elastomeric polymer chain between the last cross-link and the end of the polymer chain. This free end of the polymer does not participate in the efficient elastically recoverable process and, as a result, energy transmitted to this section of the polymer is lost. The dissipated energy leads to a pronounced hysteresis under dynamic deformation. Another source of hysteresis in vulcanized elastomeric polymers is attributed to an insufficient distribution of filler particles in the vulcanized elastomeric polymer composition. The hysteresis loss of a cross-linked elastomeric polymer composition is related to its tan δ value at 60° C. (see ISO 4664-1:2005; Rubber, Vulcanized or thermoplastic; Determination of dynamic properties—part 1: General guidance). In general, vulcanized elastomeric polymer compositions having relatively small tan δ values at 60° C. are preferred as having lower hysteresis loss. In the final tire product, this translates into a lower rolling resistance and better fuel economy.

It is generally accepted that a lower rolling resistance tire can be made at the expense of deteriorated wet grip properties. For example, if, in a random solution styrene-butadiene rubber (random SSBR), the polystyrene unit concentration is reduced with respect to the total polybutadiene unit concentration, and the 1,2-polybutadiene unit concentration is kept constant, the SSBR glass transition temperature is reduced and, as a result, both tan δ at 60° C. and tan δ at 0° C. are reduced, generally corresponding to improved rolling resistance and deteriorated wet grip performance of the tire. Similarly, if, in a random SSBR, the 1,2-polybutadiene unit concentration is reduced with respect to the total polybutadiene unit concentration, and the polystyrene unit concentration is kept constant, the SSBR glass transition temperature is reduced and, as a result, both tan δ at 60° C. and tan δ at 0° C. are reduced, generally corresponding to improved rolling resistance and deteriorated wet grip performance of the tire. Accordingly, when assessing the rubber vulcanizate performance correctly, both the rolling resistance, related to tan δ at 60° C., and the wet grip, related to tan δ at 0° C., should be monitored along with the tire heat build-up.

Hirao et al., Prog. Polym. Sci. 30 (2005) 111-182, describe the construction of multi-functionalized polymers, star-branched polymers and dendritic branched polymers.

There is a need for polymers, including modified polymers, which can be used for further optimizing dynamic properties of vulcanizates containing silica and carbon black, including low hysteresis loss and high abrasion resistance, corresponding to a high wet grip, low rolling resistance and high abrasion resistance in tires. In addition, there is a need to further decrease the vulcanizate heat build-up during thermal exposure and under mechanical stress. These needs have been met by the following invention.

SUMMARY OF THE INVENTION

In a first aspect, the present invention provides a compound of the following Formula 1:

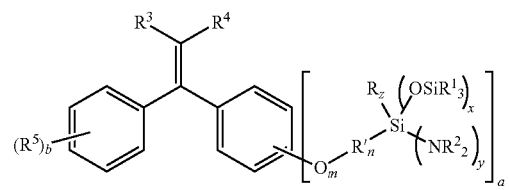

Formula 1 wherein
each R is independently selected from an optionally substituted organic group having from 1 to 12 carbon atoms, wherein R may be connected to one of the two benzene rings of Formula 1 to form a ring together with the Si atom of the aminosilyl group;
R' is an optionally substituted methylene group;
each $R^1$ is independently selected from an optionally substituted organic group having from 1 to 12 carbon atoms;
each $R^2$ is independently selected an optionally substituted organic group having from 1 to 12 carbon atoms, wherein the $R^2$ groups may be connected to each other to form a ring together with the Si-bonded nitrogen atom;
$R^3$ and $R^4$ are each independently selected from hydrogen, methyl, ethyl, propyl, butyl and vinyl;
each $R^5$ is independently selected from an optionally substituted hydrocarbon group having from 1 to 12 carbon atoms, a $C_1$-$C_6$ alkoxy group, a $C_1$-$C_6$ alkylthio group, and an amine group carrying two substituents independently selected from a $C_1$-$C_6$ alkyl group and a silyl group carrying three substituents independently selected from a $C_1$-$C_6$ alkyl group and a phenyl group;
a≥1; b≥0; a+b≤10;
m=0 or 1;
n=0 to 12;

x=0, 1 or 2; y=1, 2 or 3; z=0, 1 or 2; x+y+z=3; or x+y+z=2 when the silicon atom of the aminosilyl group is bonded twice to the benzene rings via groups R' or single bonds; with the proviso that when m=1, then n=1 to 12, and when m=n0, then x=1 or 2;
wherein the aminosilyl group(s) may be bonded to any of the two benzene rings, plural aminosilyl groups may be different from each other, and the $R^5$ group(s) may be bonded to any of the two benzene rings. The number of carbon atoms specified for an "organic group" or "hydrocarbon group" does not include those of any optional substituents.

The compound of Formula 1 can be used both as a modifying monomer in an anionic polymerization and as a precursor for a polymerization initiator.

In a second aspect, the present invention provides a polymerization initiator of the following Formula 2:

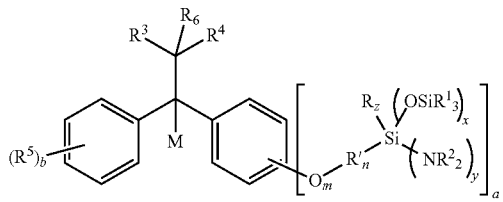

Formula 2 wherein
each R is independently selected from an optionally substituted organic group having from 1 to 12 carbon atoms, wherein R may be connected to one of the two benzene rings of Formula 1 to form a ring together with the Si atom of the aminosilyl group;
R' is an optionally substituted methylene group;
each R' is independently selected from an optionally substituted organic group having from 1 to 12 carbon atoms;
each $R^2$ is independently selected an optionally substituted organic group having from 1 to 12 carbon atoms, wherein the $R^2$ groups may be connected to each other to form a ring together with the Si-bonded nitrogen atom;
$R^3$ and $R^4$ are each independently selected from hydrogen, methyl, ethyl, propyl, butyl and vinyl;
each $R^5$ is independently selected from an optionally substituted hydrocarbon group having from 1 to 12 carbon atoms, a $C_1$-$C_6$ alkoxy group, a $C_1$-$C_6$ alkylthio group, and an amine group carrying two substituents independently selected from a $C_1$-$C_6$ alkyl group and a silyl group carrying three substituents independently selected from a $C_1$-$C_6$ alkyl group and a phenyl group;
$R^6$ is selected from $C_1$-$C_6$ alkyl, phenyl and benzyl; M is an alkali metal selected from lithium, sodium and potassium;
a≥1; b≥0; a+b≤10;
m=0 or 1;
n=0 to 12;
x=0, 1 or 2; y=1, 2 or 3; z=0, 1 or 2; x+y+z=3; or x+y+z=2 when the silicon atom of the aminosilyl group is bonded twice to the benzene rings via groups R' or single bonds; with the proviso that when m=1, then n=1 to 12, and when m=n=0, then x=1 or 2;
wherein the aminosilyl group(s) may be bonded to any of the two benzene rings, plural aminosilyl groups may be different from each other, and the $R^5$ group(s) may be bonded to any of the two benzene rings. The number of carbon atoms indicated for an "organic group" or "hydrocarbon group" does not include those of any optional substituents.

In a third aspect, the present invention provides a method of making the polymerization initiator of Formula 2 as defined in the second aspect of the invention, comprising the step of reacting (i) a compound of Formula 1 as defended in the first aspect of the invention with (ii) at least one compound of the following Formula 3:

$$R^6M \qquad \text{Formula 3}$$

wherein $R^6$ and M are as defined for Formula 2 in the second aspect of the invention.

In a fourth aspect, the invention provides a polymer, including a modified polymer, which is the reaction product of
i) a polymerization initiator of Formula 2 and
ii) one or more polymerizable monomers selected from conjugated dienes and optionally one or more polymerizable monomers selected from aromatic vinyl compounds, or
i') a polymerization initiator other than that of Formula 2,
ii') one or more polymerizable monomers selected from conjugated dienes and optionally one or more polymerizable monomers selected from aromatic vinyl compounds, and
iii') a compound of Formula 1 which is used as backbone-modifying agent and/or chain end-modifying agent.

In a fifth aspect, the invention provides a method of making the polymer of the invention, including modified polymer, comprising the step of reacting
i) a polymerization initiator of Formula 2 and
ii) one or more polymerizable monomers selected from conjugated dienes and optionally one or more polymerizable monomers selected from aromatic vinyl compounds, or
i') a polymerization initiator other than that of Formula 2,
ii') one or more polymerizable monomers selected from conjugated dienes and optionally one or more polymerizable monomers selected from aromatic vinyl compounds, and
iii') a compound of Formula 1 which is used as backbone-modifying agent and/or chain end-modifying agent.

In a sixth aspect, the invention provides a first polymer composition comprising the polymer of the invention, including modified polymer, and one or more further components selected from (i) components which are added to or formed as a result of the polymerization process used for making the polymer and (ii) components which remain after solvent removal from the polymerization process. Components which are added to the polymerization process include, in particular, oils (extender oils), stabilizers and further polymers.

In a seventh aspect, the invention provides a second polymer composition comprising the polymer of the invention, including modified polymer, and one or more fillers. The second polymer composition is the result of mechanical mixing of the polymer of the invention, including modified polymer, as obtained after solvent removal from the polymerization process, and one or more fillers and further optional components.

The first and second polymer compositions may optionally further comprise a least one vulcanizing agent.

In an eighth aspect, the invention provides a vulcanized polymer composition which is obtained by vulcanizing the first or the second polymer composition, which comprises at least one vulcanizing agent.

In a ninth aspect, the invention provides a method of making the vulcanized polymer composition of the seventh aspect, comprising the step of vulcanizing the first or second polymer composition, which comprises at least one vulcanizing agent.

In a tenth aspect, the invention provides an article comprising at least one component formed from a vulcanized polymer composition of the invention. The article may be, for example, a tire, a tire tread, a tire side wall, an automotive part, a footwear component, a golf ball, a belt, a gasket, a seal or a hose.

In accordance with the invention, it was found that the polymerization initiator of Formula 2 of the present invention is capable of providing a polymer such as SSBR exhibiting reduced heat build-up, improved of tan δ at 60° C. (rolling resistance) and improved abrasion resistance, in combination with low Mooney (CML1-4) viscosity when used in a silica-filled polymer composition, i.e. a beneficial balance of tan δ improvements at low and high temperature with only a small increase in Mooney viscosity for the silica-filled polymer compositions in comparison with the polymer Mooney viscosity. This results in good processing properties. Moreover, it was found that the compound of Formula 1 can be used as a precursor for a polymerization initiator as described herein, as a comonomer in an anionic polymerization of conjugated dienes and/or aromatic vinyl monomers, where it acts as a modifying monomer and as chain end-modifying agent.

DETAILED DESCRIPTION OF THE INVENTION

An organic group having from 1 to 12 carbon atoms, as representing R, $R^1$ and $R^2$ in Formulas 1 and 2, is a hydrocarbon group which optionally contains one or more heteroatoms (selected from N, O and S) and which is bonded through a carbon atom. Exemplary organic groups having from 1 to 12 carbon atoms and exemplary hydrocarbon groups having from 1 to 12 carbon atoms include a $C_1$-$C_{12}$ aliphatic group and a $C_3$-$C_{12}$ aromatic group. The aliphatic group may be linear, branched or cyclic and may be saturated or unsaturated, such as an alkyl group or alkenyl group. The aromatic group may be homocyclic aromatic or heterocyclic aromatic. The linear aliphatic group may be a linear $C_1$-$C_{12}$ aliphatic group and is exemplified by methyl, ethyl, n-propyl, n-butyl, n-pentyl, n-hexyl, n-heptyl, n-octyl, n-nonyl, n-decyl, n-undecyl and n-dodecyl, vinyl, propenyl and butenyl. The branched aliphatic group may be a branched $C_3$-$C_{12}$ aliphatic group and is exemplified by i-propyl, tert-butyl, sec-butyl, isopentyl, neopentyl and isohexyl, isopropenyl and isoprenyl. The cyclic aliphatic group may be a cyclic $C_3$-$C_{12}$ aliphatic group and is exemplified by cyclopropyl, cyclobutyl, cyclopentyl, cyclohexyl, cycloheptyl and cyclooctyl, cyclopentenyl, cyclohexenyl and cycloheptenyl. The homocyclic aromatic group may be a $C_6$-$C_{12}$ homocyclic aromatic group and is exemplified by phenyl and naphthyl. The heterocyclic aromatic group may be a $C_3$-$C_{12}$ heterocyclic aromatic group and is exemplified by thiazolyl, isothiazolyl, oxazolyl, isoxazolyl, furanyl, thiophenyl, pyrazinyl, pyridazinyl, pyrimidinyl, N—$C_1$-$C_7$-alkylated or N-tri($C_1$-$C_7$ hydrocarbyl)silyl-protected pyrrolyl, pyridinyl, benzoxazolyl, benzothiazolyl, benzofuranyl, cinnolinyl, phthalazinyl, chinoxalinyl, N—$C_1$-$C_7$-alkylated or N-tri($C_1$-$C_7$ hydrocarbyl)silyl-protected indolyl, chinolinyl, isochinolinyl and phenazinyl.

An organic group and hydrocarbon group as defined herein may optionally be substituted by one or more substituents, which may be the same or different. Exemplary optional substituents for the organic group and hydrocarbon group are a $C_1$-$C_{12}$ alkyl group, a $C_6$-$C_{12}$ aryl group, a $C_4$-$C_{12}$ heteroaryl group, $C_1$-$C_6$ alkoxy group, $C_1$-$C_6$ alkylthio group, a di($C_1$-$C_6$ alkyl)amino group, a diphenylamino group, a di($C_1$-$C_6$ alkyl)phosphino group, a diphenyl phosphine group, a $C_6$-$C_{12}$ aryloxy group, a $C_6$-$C_{12}$ arylthio group, a tri($C_1$-$C_6$ alkyl)silyl group, a tri($C_6$-$C_{12}$ aryl)silyl group and a tri(mixed $C_1$-$C_6$ alkyl and $C_6$-$C_{12}$ aryl)silyl group.

Aminosilyl-Substituted Diarylethene

The compound of the first aspect of the invention is an aminosilyl-substituted diarylethene of Formula 1 as defined above. It is characterized by an olefinic bond in conjugation with two benzene rings and by one or more specific aminosilyl groups bonded to any one of the two benzene rings.

By reacting the compound of the first aspect of the invention with an organometal compound $R^6M$ of Formula 3, it is possible to produce the compound (polymerization initiator) of Formula 2 according to the second aspect of the invention.

In one embodiment, each R is independently selected from $C_1$-$C_6$ alkyl, $C_2$-$C_6$ alkenyl, $C_7$-$C_{10}$ alkylaryl and $C_6$-$C_{10}$ aryl, preferably independently selected from $C_1$-$C_4$ alkyl, $C_7$ alkylaryl and $C_6$ aryl.

In one embodiment, n and m are each 0, i.e. the Si atom of the aminosilyl group is directly bonded to the benzene ring. In another embodiment, R' is methylene, m is 0 and n is 3, i.e. the Si atom of the aminosilyl group is bonded to the benzene ring through an n-propyl group (—$CH_2CH_2CH_2$—).

In one embodiment, each $R^1$ is independently selected from $C_1$-$C_{10}$ alkyl, $C_7$-$C_{10}$ alkylaryl and $C_6$-$C_{10}$ aryl, preferably independently selected from $C_1$-$C_6$ alkyl and $C_6$-$C_{10}$ aryl.

In one embodiment, each $R^2$ is independently selected from $C_1$-$C_{10}$ alkyl, $C_7$-$C_{10}$ alkylaryl and $C_6$-$C_{10}$ aryl, preferably independently selected from $C_1$-$C_8$ alkyl and $C_7$-$C_8$ alkylaryl.

In one embodiment, $R^3$ and $R^4$ are each independently selected from hydrogen, methyl and vinyl and are more preferably both hydrogen.

In one embodiment, each $R^5$ is independently selected from linear or branched $C_1$-$C_5$ alkyl, $C_7$-$C_{12}$ alkylaryl and $C_6$-$C_{12}$ aryl, preferably independently selected from $C_1$-$C_5$ alkyl, $C_7$ alkylaryl and $C_6$ aryl, more preferably independently selected from $C_1$-$C_5$ alkyl.

The aminosilyl-substituted diarylethene compound of Formula 1 contains at least one aminosilyl group on one of the benzene rings (a≥1, y≥1). In a preferred embodiment, a is 1. In another preferred embodiment, the compound of Formula 1 does not contain a group $R^5$ (b=0). The group linking the aminosilyl substituent and the benzene ring can be a single bond (m=n=0) or an alkyl chain having up to 12 carbon atoms (R'=methylene, m=0 and n=1-12), preferably a single bond or an n-propyl chain (i.e. m=n=0, or R'=methylene and m=0 and n=3). In the case of n being at least 1, the aminosilyl substituent is electronically decoupled from the aromatic system of the benzene ring, which may enhance the stability of the anion formed in the compound of Formula 2 and may reduce the influence of the aminosilyl group on the polymerization kinetics. When m=n=0, then the aminosilyl group carries at least one siloxy group (x=1 or 2). In this case, it is preferred that a=1, b=0, x=1 or 2, y=1 or 2 and z=0 or 1, and it is even more preferred that a=1 or 2, b=0, x=1, y=1 and z=1.

In a preferred embodiment of the compound of Formula 1, each R is independently selected from $C_1$-$C_5$ alkyl and $C_6$ aryl, each $R^1$ is independently selected from $C_1$-$C_4$ alkyl and $C_6$ aryl, each $R^2$ is independently selected from $C_1$-$C_8$ alkyl and $C_7$-$C_{10}$ alkylaryl, $R^3$ and $R^4$ are each hydrogen, each $R^5$ is independently selected from $C_1$-$C_4$ alkyl, R' is methylene, a=1 or 2, b=0 or 1, m=0, n=0, 1, 2 or 3, x=1 or 2, y=1 or 2 and z=0 or 1.

Preferred compounds of Formula 1 are exemplified by the following ones:
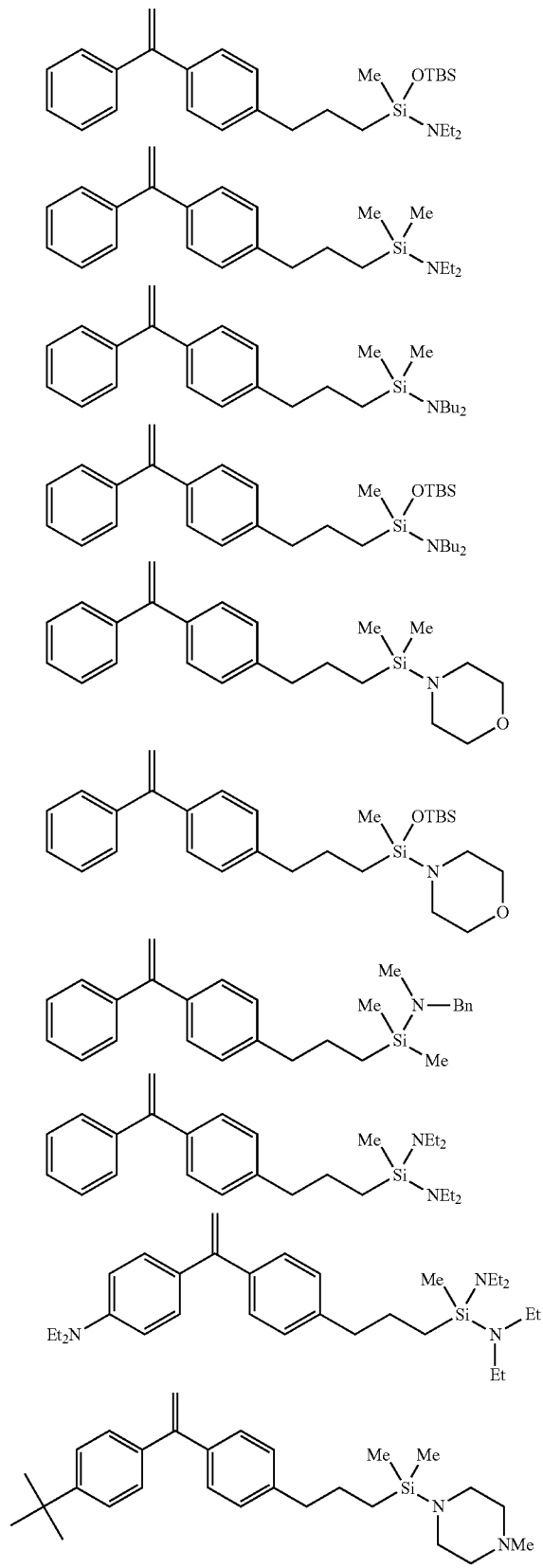
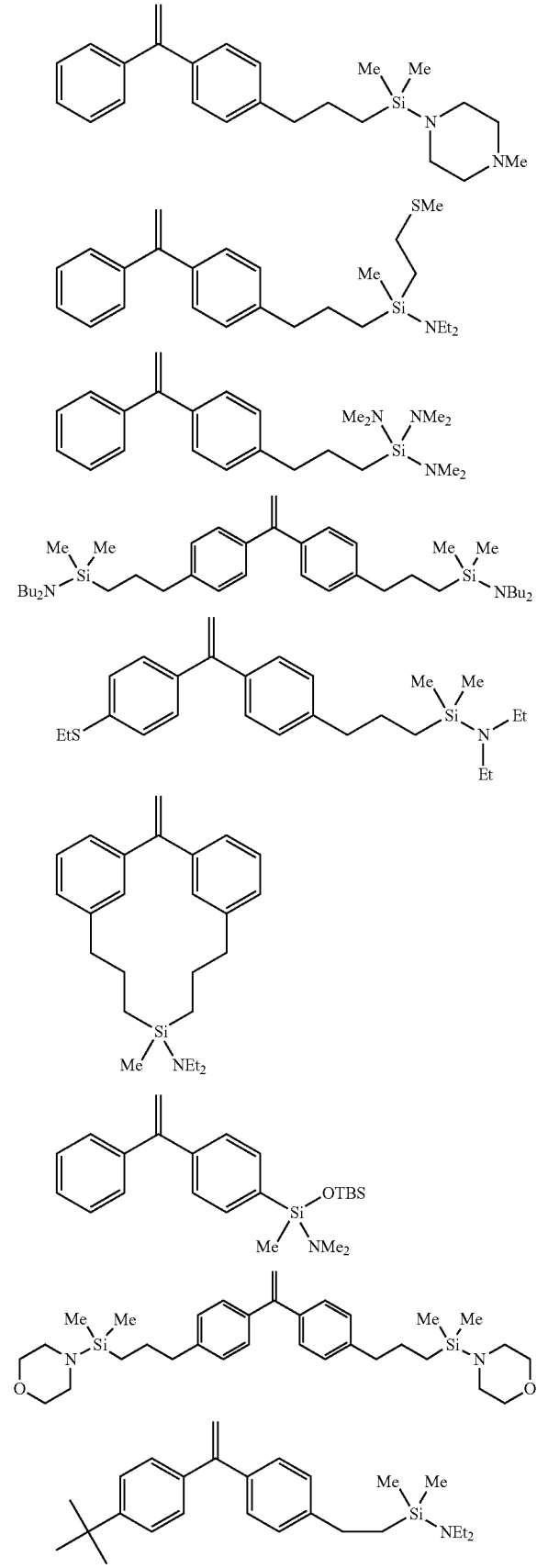

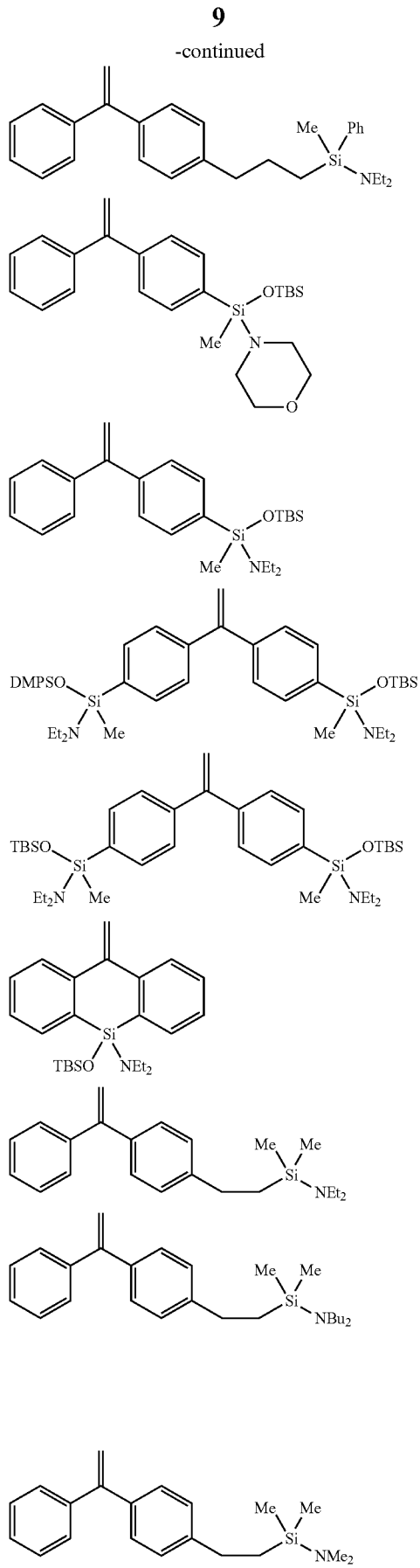

Polymerization Initiator

The polymerization initiator of the second aspect of the invention is a compound of Formula 2 as defined above. The polymerization initiator of the invention is characterized by one or more specific aminosilyl groups bonded to one or both of the two benzene rings and includes a metal atom M. The alkali metal M will usually form a metal cation, and the counter-electron (electron pair) may be delocalized over the two benzene rings.

In the initiator of Formula 2, R, R', $R^1$, $R^2$, $R^3$, $R^4$, $R^5$, a, b, m, n, x, y and z and preferred embodiments thereof are defined as for the compound of Formula 1 above.

$R^6$ is selected from $C_1$-$C_6$ alkyl, phenyl and benzyl and is preferably selected from methyl, n-butyl, sec-butyl, tert-butyl and phenyl, more preferably n-butyl. M is selected from lithium, sodium and potassium and is preferably lithium.

In a preferred embodiment of the initiator of Formula 2, each R is independently selected from $C_1$-$C_5$ alkyl and $C_6$ aryl, each $R^1$ is independently selected from $C_1$-$C_4$ alkyl and $C_6$ aryl, each $R^2$ is independently selected from $C_1$-$C_8$ alkyl and $C_7$-$C_{10}$ alkylaryl, $R^3$ and $R^4$ are each hydrogen, each $R^5$ is independently selected from $C_1$-$C_4$ alkyl, $R^6$ is selected from methyl, ethyl, tert-butyl, n-butyl, sec-butyl, phenyl and benzyl, M is lithium, a=1 or 2, b=0 or 1, m=0 and R' is methylene and n=1, 2 or 3, x=0 or 1, y=1 or 2 and z=0 or 1.

Preferred initiators of Formula 2 are exemplified by the reaction products of n-butyl lithium with the explicit examples (chemical structures) of the compound of Formula 1 shown above.

Method of Making the Polymerization Initiator

The polymerization initiators of Formula 2 of the invention are produced, as the third aspect of the invention, from the corresponding compounds of Formula 1 which contain an olefinic bond in conjugation with two benzene rings.

The method of making the polymerization initiator of Formula 2 comprises the step of reacting a compound of Formula 1 with at least one compound of Formula 3. The reaction is usually carried out in an organic solvent or a mixture of two or more organic solvents which does not deactivate the polymerization initiator of Formula 2 when subsequently used in the polymerization process. Suitable organic solvents include aliphatic and aromatic hydrocarbon solvents such as propane, butane, pentane, hexane, cyclohexane, methylcyclohexane, heptane, butene, propene, pentene, hexane, octane, benzene, toluene, ethylbenzene and xylene. The reaction can optionally be carried out in the additional presence of Lewis bases such as triethylamine, 1,4-diazabicyclo[2.2.2]octane (DABCO), N,N'-dimethylpiperazine, tetramethylethylenediamine (TMEDA), diethylether, dioxane, ethyleneglycol dimethylether (glyme), diglyme, and crown ethers such as 12-crown-4, 15 crown-5 and 18-crown-6.

The reaction is usually carried out at a ratio of compound of Formula 3 to compound of Formula 1 in terms of mole equivalents of from 0.5 to 4 (0.5:1 to 4:1), preferably from 0.8 to 1.5 and even more preferably from 0.9 to 1.1. The reaction is usually carried out for a period of from 2 seconds to 3 days, preferably from 5 seconds to 2 days, even more preferably from 10 seconds to 10 hours, at a temperature ranging from −10° C. to 130° C., preferably from 0° C. to 100° C. and even more preferably from 20° C. to 50° C.

For increasing the storage stability (shelf life) of the polymerization initiator, it is possible to contact the resulting reaction mixture containing the polymerization initiator and including the metal M with a limited amount of one or more polymerizable monomers selected from conjugated dienes and aromatic vinyl compounds, preferably selected from styrene, butadiene and isoprene. For this purpose, an amount of up to 1000 equivalents, preferably up to 200 equivalents, most preferably up to 75 equivalents of polymerizable monomer per alkali metal equivalent is suitably used.

Polymer

The polymer of the fourth aspect of the invention, including modified polymer, is the reaction product of:
  i) a polymerization initiator of Formula 2 and
  ii) one or more polymerizable monomers selected from conjugated dienes and optionally one or more polymerizable monomers selected from aromatic vinyl compounds, or
  i') a polymerization initiator other than that of Formula 2,
  ii') one or more polymerizable monomers selected from conjugated dienes and optionally one or more polymerizable monomers selected from aromatic vinyl compounds, and
  iii') a compound of Formula 1 which is used as backbone-modifying agent and/or chain end-modifying agent.

A polymerization initiator other than that of Formula 2 can be any conventionally known initiator for anionic polymerization, such as n-butyllithium.

Generally, for producing a polymer of the invention, one or a mixture of two or more polymerization initiators of the invention or compounds of Formula 1 may be used.

The polymerization initiator of Formula 2 may be reacted with a fraction of the total amount of monomers required for making the desired polymer and may then be stored for an amount of time, for example from seconds to weeks, before further reacting it with the remaining amount of monomers to complete the polymerization process. In one embodiment, the fraction of the total amount of monomers is from 1 to 40 monomer equivalents based on the amount of polymerization initiator.

The polymer of the invention can be a modified polymer which is terminally (chain end-) and/or backbone-modified. For providing a backbone-modified polymer, the polymerization is carried out in the presence of one or more backbone-modifying agents, such as a compound of Formula 1, which are added continuously or intermittently as the polymerization proceeds. For providing a chain end-modified polymer, one or more chain end-modifying agents as described below and including a compound of Formula 1 are added following the polymerization reaction.

Moieties resulting from the process of chain end modification using chain end-modifying agents having a terminal trihydrocarbylsilyl group, including trialkylsilyl, trialkylarylsilyl and triarylsilyl; trihydrocarbyistannyl group, including trialkylstannyl, trialkylarylstannyl and triarylstannyl; dihydrocarbylsilendiyl group, including dialkylsilendeyl, dialkylarylsilendiyl and diarylsilendiyl; or dihydrocarbylstannendiyl group, including dialkylstannendiyl, dialkylarylstannendiyl and diarylstannendiyl, are believed to function as protective groups, which prevent unintended subsequent reaction of the polymer chain. Such protective groups may be removed by exposure to a compound containing a reactive hydroxyl group (—OH), such as water, alcohols, anionic acids or organic acids (for example hydrochloric acid, sulfuric acid or carboxylic acids). Such conditions are typically present during vulcanization. In those cases where the terminal group of the chain end-modifying agent is sulfide-linked, the exposure to a reactive hydroxyl group and deprotection will result in the formation of an unprotected thiol group (—SH) as the terminal group of the polymer chain. Depending on the work-up conditions for the modified polymer (e.g., steam stripping), both the unprotected modified and the protected modified polymer may be present.

It is believed that certain terminal groups of the polymer, such as an unprotected thiol group, are reactive towards fillers such as silica and/or carbon black, which may result in a more homogeneous distribution of the filler within a polymer composition.

The reaction product as a chain end-modified polymer typically contains silanol groups and alkoxysilyl groups in a total amount from 0.0001 to 3.00 mmol/gram of polymer, preferably from 0.0005 to 1.8 mmol/gram, more preferably from 0.0010 to 1.0 mmol/gram and even more preferably from 0.0020 to 0.2 mmol/gram.

The reaction product as a chain end-modified polymer preferably contains sulfide groups (in the form of thiol groups and/or sulfide-linked protective groups) in a total amount of from 0.0001 to 0.80 mmol/gram of polymer, preferably from 0.0005 to 0.50 mmol/gram, more preferably from 0.0010 to 0.30 mmol/gram and even more preferably from 0.0020 to 0.20 mmol/gram of polymer.

For most applications, the polymer of the invention is preferably a homopolymer derived from a conjugated diolefin, a copolymer derived from two or more conjugated diolefins or from a conjugated diolefin and an aromatic vinyl monomer, or a terpolymer of one or two types of conjugated diolefins with one or two types of aromatic vinyl compounds. Examples of particularly useful polymers include homopolymers of butadiene or isoprene and random or block co- and terpolymers of butadiene, isoprene and styrene, especially a random copolymer of butadiene with isoprene and a random or block copolymer of butadiene with styrene.

Although there are no specific limitations regarding the amount of aromatic vinyl monomer used in the polymer, for most applications aromatic vinyl monomers constitute from 1 to 60%, preferably from 2 to 55% and more preferably from 5 to 50% by weight, based on the total weight of the polymer. An amount of less than 2% by weight may lead to a deteriorated balance of rolling resistance, wet skid and abrasion resistance and to reduced tensile strength, whereas an amount of more than 60% by weight may lead to increased hysteresis loss. The polymer may be a block or random copolymer of an aromatic vinyl monomer, and preferably 40% by weight or more of the aromatic vinyl monomer units are linked singly, and 10% by weight or less are polymeric "blocks" of eight or more aromatic vinyl monomers linked successively (the length of successively linked aromatic vinyl units can be measured by an ozonolysis-gel permeation chromatography method developed by Tanaka et al. (Polymer, Vol. 22, pp. 1721-1723 (1981)). Copolymers outside this range tend to exhibit increased hysteresis loss.

Although there are no specific limitations regarding the content of 1,2-bonds and/or 3,4-bonds (hereinafter called "vinyl bond content") of the conjugated diolefin portion of the polymer, for most applications the vinyl bond content is less than 90% by weight, particularly preferably less than 80% by weight (based on the total weight of the polymer). If the vinyl content in the polymer exceeds 90% by weight, the resulting product may exhibit deteriorated tensile strength and abrasion resistance and a relatively large hysteresis loss.

Monomers

The monomers used in the preparation of the polymer of the invention are one or more polymerizable monomers selected from conjugated dienes and optionally one or more polymerizable monomers selected from aromatic vinyl compounds. Additionally and optionally, one or more other comonomers may be used.

Suitable conjugated dienes include conjugated dienes, such as 1,3-butadiene, 2-alkyl-1,3-butadiene, isoprene (2-methyl-1,3-butadiene), 2,3-dimethyl-1,3-butadiene, 1,3-pentadiene, 2,4-hexadiene, 1,3-hexadiene, 1,3-heptadiene, 1,3-octadiene, 2-methyl-2,4-pentadiene, cyclopentadiene, 2,4-hexadiene and 1,3-cyclooctadiene and a combination of two or more thereof. 1,3-butadiene and isoprene are preferred conjugated dienes, and 1,3-butadiene is a particularly preferred one.

Suitable aromatic vinyl compounds include styrene, $C_{1-4}$ alkyl-substituted styrene, such as 2-methylstyrene, 3-methylstyrene, 4-methylstyrene, 2,4-dimethylstyrene, 2,4,6-trimethylstyrene, α-methylstyrene and stilbene, 2,4-diisopropylstyrene, 4-tert-butylstyrene, vinyl benzyl dimethylamine, (4-vinylbenzyl)dimethyl aminoethyl ether, N,N-dimethylaminoethyl styrene, tert-butoxystyrene, vinylpyridine and compounds of Formula 1 and a combination of two or more aromatic vinyl compounds. Styrene is a particularly preferred aromatic vinyl compound.

In addition to the above-mentioned conjugated dienes and aromatic vinyl compounds, it is possible to make use of one or more comonomers selected from olefins and nonconjugated diolefins, such as $C_2$-$C_{20}$ α-olefins and non-conjugated $C_4$-$C_{20}$ diolefins, especially norbornadiene, ethylidenenorbornene, 1,4-hexadiene, 1,5-hexadiene, 1,7-octadiene, 4-vinylcyclohexene and divinylbenzene including 1,2-divinylbenzene, 1,3-divinylbenzene and 1,4-divinylbenzene. Divinylbenzenes in particular will act as a branching agent. Furthermore, one or more compounds of Formula 1 may be used as comonomers for the purpose of backbone modification of the polymer.

In one embodiment, the amount of divinylbenzene, including 1,2-divinylbenzene, 1,3-divinylbenzene and 1,4-divinylbenzene, is 1 mol % or less (based on the total molar amount of the monomers used to make the polymer). In another embodiment, the amount of compounds of Formula 1 is 5 mol % or less, preferably less than 1 mol %.

Chain End-Modifying Agents

One or more chain end-modifying agents may be used in the polymerization reaction of the present invention for further controlling polymer properties by reacting with the terminal ends of the polymer chains in the polymer of the invention. Generally, silane-sulfide omega chain end-modifying agents such as disclosed in WO 2007/047943, WO 2009/148932, U.S. Pat. No. 6,229,036, US 2013/0131263 and EP 2 085 419, each incorporated herein by reference in its entirety, can be used for this purpose. Other chain end-modifying agents suitable for use in the present invention are those disclosed in WO 2014/040640 and the silane sulfide modifiers described in WO 2014/040639. Furthermore, in accordance with the present invention, it is also possible to make use of one or more compounds of Formula 1 as a chain end-modifying agent.

The chain end-modifying agents may be added intermittently (at regular or irregular intervals) or continuously during the polymerization, but are preferably added at a conversion rate of the polymerization of more than 80 percent and more preferably at a conversion rate of more than 90 percent. Preferably, a substantial amount of the polymer chain ends is not terminated prior to the reaction with the chain end-modifying agent; that is, living polymer chain ends are present and are capable of reacting with the modifying agent.

Randomizer Agents

Randomizer compounds as conventionally known in the art (also known as polar coordinator compounds) may optionally be added to the monomer mixture or polymerization reaction, in order to adjust the microstructure (i.e. the content of vinyl bonds) of the conjugated diene part of the polymer, or to adjust the composition distribution of any aromatic vinyl monomer and of the vinyl bonds in the polymer chain. A combination of two or more randomizer compounds may be used. Randomizer compounds useful in the invention are generally exemplified by Lewis base compounds. Suitable Lewis bases for use in the present invention are, for example, ether compounds such as diethyl ether, di-n-butyl ether, ethylene glycol diethyl ether, ethylene glycol dibutyl ether, diethylene glycol dimethyl ether, propylene glycol dimethyl ether, propylene glycol diethyl ether, propylene glycol dibutyl ether, ($C_1$-$C_8$ alkyl)tetrahydrofurylethers (including methyltetrahydrofurylether, ethyltetrahydrofurylether, propyltetrahydrofurylether, butyltetrahydrofurylether, hexyltetrahydrofurylether and octyltetrahydrofurylether), tetrahydrofuran, 2,2-(bistetrahydrofurfuryl)propane, bistetrahydrofurfurylformal, methyl ether of tetrahydrofurfuryl alcohol, ethyl ether of tetrahydrofurfuryl alcohol, butyl ether of tetrahydrofurfuryl alcohol, α-methoxytetrahydrofuran, dimethoxybenzene and dimethoxyethane, and tertiary amines such as triethylamine, pyridine, N,N,N',N'-tetramethyl ethylenediamine, dipiperidinoethane, methyl ether of N,N-diethylethanolamine, ethyl ether of N,N-diethylethanolamine, N,N-diethylethanolamine and dimethyl N,N-tetrahydrofurfuryl amine. Na and K alcoholates can be added to increase the reaction rate. Examples of preferred randomizer compounds are identified in WO 2009/148932, incorporated herein by reference in its entirety. The randomizer compound will typically be added at a molar ratio of randomizer compound to initiator compound of from 0.012:1 to 10:1, preferably from 0.1:1 to 8:1 and more preferably from 0.25:1 to about 6:1.

Coupling Agents

For further controlling polymer molecular weight and polymer properties, a coupling agent ("linking agent") can be used as an optional component in the process of the invention. A coupling agent will reduce hysteresis loss by reducing the number of free chain ends of the elastomeric polymer and/or reduce the polymer solution viscosity, compared with non-coupled essentially linear polymer macromolecules of identical molecular weight. Coupling agents such as tin tetrachloride may functionalize the polymer chain end and react with components of an elastomeric composition, for example with a filler or with unsaturated portions of a polymer. Exemplary coupling agents are described in U.S. Pat. No. 3,281,383, U.S. Pat. No. 3,244,664 and U.S. Pat. No. 3,692,874 (e.g., tetrachlorosilane); U.S. Pat. No. 3,978,103, U.S. Pat. Nos. 4,048,206, 4,474,908 and U.S. Pat. No. 6,777,569 (blocked mercaptosilanes); U.S. Pat. No. 3,078,254 (multi-halogen-substituted hydrocarbon, such as 1,3,5-tri(bromo methyl) benzene); U.S. Pat. No. 4,616,069 (tin compound and organic amino or amine compound); and U.S. Pat. No. 2005/0124740. Generally, the chain end-modifying agent is added before, during or after the addition of the coupling agent, and the modification reaction is preferably carried out after the addition of the coupling agent. The total amount of coupling agents used will influence the Mooney viscosity of the coupled polymer and is typically in the range of from 0.001 to 4.5 milliequivalents per 100 grams of the elastomeric polymer, for example 0.01 to about 1.5 milliequivalents per 100 grams of polymer.

Method of Making Polymer

The method of making the polymer according to the fifth aspect of the invention comprises the steps of reacting i) a polymerization initiator of Formula 2 and ii) one or more polymerizable monomers selected from conjugated dienes and optionally one or more polymerizable monomers selected from aromatic vinyl compounds, or a polymerization initiator other than that of Formula 2, ii') one or more polyermizable monomers selected from conjugated dienes and optionally one or more polymerizable monomers selected from aromatic vinyl compounds, and iii') a compound of Formula 1 which is used as backbone-modifying agent and/or chain end-modifying agent.

A polymerization initiator other than that of Formula 2 can be any conventionally known initiator for anionic polymerization, such as n-butyllithium.

In a preferred embodiment, the method of making the modified polymer comprises the steps of firstly reacting a polymerization initiator of Formula 2 with one or more polymerizable monomers selected from conjugated dienes and optionally one or more polymerizable monomers selected from aromatic vinyl compounds, thus forming an anionic living polymer, and further reacting the anionic living polymer with a chain end-modifying agent as described above, thus forming a chain end-modified polymer.

The method of making the polymer is conventionally carried out in a polymerization solvent as a solution polymerization, wherein the polymer formed is substantially soluble in the reaction mixture, or as a suspension/slurry polymerization, wherein the polymer formed is substantially insoluble in the reaction medium. Suitable polymerization solvents include non-polar aliphatic and non-polar aromatic solvents, preferably hexane, heptane, butane, pentane, isopar, cyclohexane, toluene and benzene. The solution polymerization normally takes place at lower pressures, preferably below 10 MPa, preferably in a temperature range of from 0 to 120° C. The polymerization is generally conducted under batch, continuous or semi-continuous polymerization conditions.

Generally applicable information about the polymerization technologies including polymerization initiator compounds; polar coordinator compounds and accelerators, each to increase the reactivity of the initiator, to randomly arrange aromatic vinyl compounds, to randomly arrange 1,2-polybutadiene or 1,2-polyisoprene or 3,4-polyisoprene units introduced in the polymer; the amounts of each compound; monomer(s); and suitable process conditions are described in WO 2009/148932, fully incorporated herein by reference.

Polymer Compositions

The first polymer composition according to the sixth aspect of the invention comprises the polymer of the invention, including modified polymer, and one or more further components selected from (i) components which are added to or formed as a result of the polymerization process used for making the polymer and (ii) components which remain after solvent removal from the polymerization process. Generally, the first polymer composition is the solvent-free result of the method of making the polymer, further comprising components selected from oils (extender oils), stabilizers and further (non-inventive) polymers. Suitable oils are as defined herein. The further polymers can be made separately, for example in a different polymerization reactor, in solution and can be added to the reactor prior to completion of the polymer manufacturing process for the polymer.

In the first composition, the polymer present is preferably composed of at least 15% by weight of the polymer as obtained in the polymerization reaction, more preferably at least 30% by weight and even more preferably at least 45% by weight. The remaining amount of polymer is composed of the further polymers mentioned above. Examples of suitable polymers are identified in WO 2009/148932 and preferably include styrene-butadiene copolymer, natural rubbers, polyisoprene and polybutadiene. It is desirable that such further polymers have a Mooney viscosity (ML 1+4, 100° C. as measured in accordance with ASTM D 1646 (2004)) in the range of from 20 to 150, preferably from 30 to 100.

The second polymer composition according to the seventh aspect of the invention comprises the polymer of the invention, including modified polymer, and one or more fillers. The second polymer composition is typically the result of a mechanical mixing process involving the polymer of the invention and one or more fillers. It typically includes components which are added to and mechanically mixed with the polymer or first polymer composition.

The first and second polymer compositions may optionally further comprise a least one vulcanizing agent as defined further below.

The second polymer composition comprising filler can be prepared by kneading the first polymer composition, optionally comprising one or more components selected from oils, stabilizers and further polymers, and one or more fillers in a kneader at 140 to 180° C.

Alternatively, the second polymer composition can be prepared by kneading the first polymer composition and one or more fillers in a kneader at 140 to 180° C. to form a "first stage" second composition. The formation of the "first stage" second composition may involve one or more mixing steps, preferably 2 to 7 mixing steps. After cooling, vulcanizing agents such as sulfur, vulcanizing accelerators, optionally zinc oxide and the like are added to the "first stage" second composition, and the resulting "second stage" second composition is blended using an internal mixer related to Banbury or intermesh rotors or open roll mill to form the desired shape.

Oils

One or more oils, including liquid polymers, may be used in combination with the uncrosslinked polymer to reduce viscosity or Mooney values or to improve processability of the first polymer composition and various performance properties of the (vulcanized) second polymer compositions.

Oils and liquid polymers can be added to the polymer prior to the end of the polymer preparation process and as a separate component of the first or second polymer composition preparation process in accordance with the present teachings. For representative examples and classification of oils see WO 2009/148932 and US 2005/0159513, each of which is incorporated herein by reference in its entirety. For liquid polymers see examples in U.S. Pat. No. 8,030,406 B2 and U.S. Pat. No. 7,868,081 B2. Exemplary oils include, for instance, conventionally known extender oils such as aromatic, naphthenic and paraffinic extender oils, for example MES (mild extraction solvate), TDAE (treated distillate aromatic extract), rubber-to-liquid (RTL) oils, biomass-to-liquid (BTL) oils, factices, extender resins or liquid polymers (such as liquid BR) having a median molecular weight (determined via GPC according to BS ISO 11344:2004) of from 500 to 20000 g/mol. In addition, native oils, including vegetable oils, can be used as extender oils. Representative oils also include functionalized variations of these oils, particularly epoxidized or hydroxylated oils. The oils may contain varying concentrations of polycyclic aromatic compounds, paraffinics, naphthenics and aromatics and may have different glass transition temperatures.

The polymer compositions may contain one or more oils in a total amount of from 0 to 70 phr, preferably 0.1 to 60 phr, more preferably 0.1 to 50 phr. When liquid polymers are used as extender oils in the polymer compositions of the present invention, they are not taken into account when calculating the composition of the polymer matrix.

Processing Aids

Processing aids can optionally be added to the first polymer composition. They are usually added for reducing the viscosity. As a result, the mixing period is decreased and/or the number of mixing steps is reduced and, consequently, less energy is consumed and/or a higher throughput in the course of the rubber compound extrusion process is achieved. Representative processing aids are described in *Rubber Handbook, SGF, The Swedish Institution of Rubber Technology* 2000 and in Werner Kleemann, Kurt Weber, *Elastverarbeitung-Kennwerte and Berechnungsmethoden*, Deutscher Verlag für Grundstoffindustrie (Leipzig, 1990), each of which is incorporated herein by reference in its entirety. Examples of representative processing aids include in particular:

(A) fatty acids, including oleic acid, priolene, pristerene and stearic acid;

(B) fatty acid salts, including Aktiplast GT, PP, ST, T, T-60, 8, F; Deoflow S; Kettlitz Dispergator FL, FL Plus; Dispergum 18, C, E, K, L, N, T, R; Polyplastol 6, 15, 19, 21, 23; Struktol A50P, A60, EF44, EF66, EM16, EM50, WA48, WB16, WB42, WS180, WS280 and ZEHDL;

(C) dispersing agents, including Aflux 12, 16, 42, 54, 25; Deoflow A, D; Deogum 80; Deosol H; Kettlitz Dispergator DS, KB, OX; Kettlitz-Mediaplast 40, 50, Pertac/GR; Kettlitz-Dispergator SI; Struktol FL and WB 212; and (D) dispersing agents for highly active white fillers, including Struktol W33 and WB42.

Fillers

The second composition of the invention comprises one or more fillers, which serve as reinforcement agents. Examples of suitable fillers include carbon black (including electroconductive carbon black), carbon nanotubes (CNT) (including discrete CNT, hollow carbon fibers (HCF) and modified CNT carrying one or more functional groups, such as hydroxyl, carboxyl and carbonyl groups), graphite, graphene (including discrete graphene platelets), silica, carbon-silica dual-phase filler, clays (layered silicates, including exfoliated nanoclay and organoclay), calcium carbonate, magnesium carbonate, lignin, amorphous fillers, such as glass particle-based fillers, starch-based fillers, and combinations thereof. Further examples of suitable fillers are described in WO 2009/148932 which is fully incorporated herein by reference.

Examples of suitable carbon black include the one conventionally manufactured by a furnace method, for example having a nitrogen adsorption specific surface area of 50-200 $m^2/g$ and DBP oil absorption of 80-200 ml/100 grams, such as carbon black of the FEF, HAF, ISAF or SAF class, and electroconductive carbon black. In some embodiments, high agglomeration-type carbon black is used. Carbon black is typically used in an amount of from 2 to 100 parts by weight, or 5 to 100 parts by weight, or 10 to 100 parts by weight, or 10 to 95 parts by weight per 100 parts by weight of the total polymer.

Examples of suitable silica fillers include wet process silica, dry process silica and synthetic silicate-type silica. Silica with a small particle diameter and high surface area exhibits a high reinforcing effect. Small diameter, high agglomeration-type silica (i.e. having a large surface area and high oil absorptivity) exhibits excellent dispersibility in the polymer composition, resulting in superior processability. An average particle diameter of silica in teams of the primary particle diameter may be from 5 to 60 nm, or 10 to 35 nm. The specific surface area of the silica particles (measured by the BET method) may be from 35 to 300 $m^2/g$. Silica is typically used in an amount of from 10 to 100 parts by weight, or 30 to 100 parts by weight, or 30 to 95 parts by weight per 100 parts by weight of the total polymer.

Silica fillers can be used in combination with other fillers, including carbon black, carbon nanotubes, carbon-silica dual-phase-filler, graphene, graphite, clay, calcium carbonate, magnesium carbonate and combinations thereof.

Carbon black and silica may be added together, in which case the total amount of carbon black and silica is from 30 to 100 parts by weight or 30 to 95 parts by weight per 100 parts by weight of the total polymer.

Carbon-silica dual-phase filler is so called silica-coated carbon black made by coating silica on the surface of carbon black and commercially available under the trademark CRX2000, CRX2002 or CRX2006 (products of Cabot Co.). Carbon-silica dual-phase filler is added in the same amounts as described above with respect to silica.

Silane Coupling Agents

In some embodiments, a silane coupling agent (used for compatibilization of polymer and fillers) is added to the composition comprising the polymer of the invention and silica, layered silicate (such as magadiite) or carbon-silica dual-phase filler. The typical amount of a silane coupling agent added is from about 1 to about 20 parts by weight and, in some embodiments, from about 5 to about 15 parts by weight for 100 parts by weight of the total amount of silica and/or carbon-silica dual-phase filler.

Silane coupling agents can be classified according to *Fritz Röthemeyer, Franz Sommer: Kautschuk Technologie*, (Carl Hanser Verlag 2006):

(A) bifunctionalized silanes, including Si230 ((EtO)$_3$Si(CH$_2$)$_3$Cl), Si225 ((EtO)$_3$SiCH=CH$_2$), A189 ((EtO)$_3$Si(CH$_2$)$_3$SH), [(EtO)$_3$Si(CH$_2$)$_3$S$_x$(CH$_2$)$_3$Si(OEt)$_3$] with x=3.75 (Si69) or 2.35 (Si75), Si264 ((EtO)$_3$Si—(CH$_2$)$_3$SCN) and Si363 ((EtO)Si((CH$_2$—CH$_2$—O)$_5$(CH$_2$)$_{12}$CH$_3$)$_2$(CH$_2$)$_3$SH)) (Evonic Industries AG), 3-octanoylthio-1-propyltriethoxysilane (NXT) and (B) monofunctional silanes, including Si203 ((EtO)$_3$—Si—C$_3$H$_7$) and Si208 ((EtO)$_3$—Si—C$_8$H$_{17}$).

Further suitable examples of silane coupling agents are given in WO 2009/148932 and include bis-(3-hydroxy-dimethylsilyl-propyl)tetrasulfide, bis-(3-hydroxy-dimethylsilyl-propyl) disulfide, bis-(2-hydroxy-dimethylsilyl-ethyl) tetrasulfide, bis-(2-hydroxy-dimethylsilyl-ethyl)disulfide, 3-hydroxy-dimethylsilyl-propyl-N,N-dimethylthiocarbamoyl tetrasulfide and 3-hydroxy-dimethylsilyl-propylbenzothiazole tetrasulfide.

Vulcanizing Agents

Any vulcanizing agent conventionally used in the manufacture of rubber products can be used in the invention, and a combination of two or more vulcanizing agents may be used.

Sulfur, sulfur-containing compounds acting as sulfur donors, sulfur accelerator systems and peroxides are the most common vulcanizing agents. Examples of sulfur-containing compounds acting as sulfur donors include dithiodimorpholine (DTDM), tetramethylthiuram disulfide (TMTD), tetraethylthiuram disulfide (TETD) and dipentamethylthiuram tetrasulfide (DPTT). Examples of sulfur accelerators include amine derivates, guanidine derivates, aldehydeamine condensation products, thiazoles, thiuram sulfides, dithiocarbarnates and thiophosphates. Examples of peroxides include di-tert.-butyl-peroxides, di-(tert.-butyl-peroxy-trimethyl-cyclohexane), di-(tert.-butyl-peroxy-isopropyl-)benzene, dichloro-benzoylperoxide, dicumylperoxides, tert.-butyl-cumyl-peroxide, dimethyl-di(tert.-butyl-peroxy)hexane, dimethyl-di(tert.-butyl-peroxy)hexine and butyl-di(tert.-butyl-peroxy)valerate (*Rubber Handbook, SGF, The Swedish Institution of Rubber Technolgy* 2000).

Further examples and additional information regarding vulcanizing agents can be found in Kirk-Othmer, *Encyclopedia of Chemical technology* 3$^{rd}$, Ed., (Wiley Interscience, N.Y. 1982), volume 20, pp. 365-468, (specifically "Vulcanizing Agents and Auxiliary Materials" pp. 390-402).

A vulcanizing accelerator of the sulfene amide-type, guanidine-type or thiuram-type can be used together with a vulcanizing agent as required. Other additives such as zinc white, vulcanization auxiliaries, aging preventives, processing adjuvants and the like may optionally be added. A vulcanizing agent is typically added to the polymer composition in an amount of from 0.5 to 10 parts by weight or, in some embodiments, 1 to 6 parts by weight per 100 parts by weight of the total polymer. Examples of vulcanizing accelerators and amount thereof added with respect to the total polymer are given in WO 2009/148932.

Sulfur accelerator systems may or may not contain zinc oxide. Zinc oxide is preferably used as a component of the sulfur accelerator system.

Vulcanized Polymer Composition

The vulcanized polymer composition according to the eighth aspect of the invention is obtained by vulcanizing the first or the second polymer composition, which comprises at least one vulcanizing agent. Since the vulcanized elastomeric polymer compositions of the invention exhibit low rolling resistance, low dynamic heat build-up and superior wet skid performance, they are well suited for use in manufacturing tires, tire treads, side walls and tire carcasses as well as other industrial products such as belts, hoses, vibration dampers and footwear components.

The vulcanized polymer composition is the result of a reactive polymer-polymer crosslink-forming process which is performed on (i) a mixture of the polymer and at least one vulcanizing agent, (ii) the first polymer composition comprising at least one vulcanizing agent, or (iii) the second polymer composition comprising at least one vulcanizing agent. Therefore, the reactive process converts an essentially uncrosslinked polymer or an essentially uncrosslinked polymer composition, particularly a first polymer composition or second polymer composition each containing at least one vulcanizing agent, into a vulcanized (or crosslinked) polymer composition.

The cross-linked (vulcanized) polymer composition of the invention exhibits reduced heat build-up, increased rebound resilience at 60° C. and a good balance of physical properties, including one or more of the following: abrasion resistance, tensile strength, modulus and tear, while a composition comprising the uncrosslinked polymer (prior to vulcanization) maintains good processing characteristics. The composition is useful in preparing tire treads having lower rolling resistance, and lower heat build-up, while maintaining good wear properties.

For a vulcanized polymer, the gel content is preferably greater than 50 weight percent, more preferably greater than 75 weight percent and even more preferably greater than 90 weight percent, based on the weight of the polymer. Gel content can be determined by dissolving 0.2 grams of polymer in 150 ml of toluene for 24 hours at ambient temperature, separating the insolubles, drying the insolubles and measuring the amount of insolubles.

The invention also provides an article comprising at least one component formed from a vulcanized polymer composition of the invention. The article may be a tire, a tire tread, a tire side wall, an automotive part, a footwear component, a golf ball, a belt, a gasket, a seal or a hose.

For producing vehicle tires, the following further polymers are of particular interest for use in combination with the polymer of the invention: natural rubber; low cis polybutadiene (LCBR) comprising less than 20 percent by weight of 1,2-polybutadiene, emulsion SBR (ESBR) and solution SBR (SSBR) rubbers with a glass transition temperature above −50° C.; polybutadiene rubber with a high cis-1,4-unit content (>90%), such as obtained by using catalysts based on nickel, cobalt, titanium, vanadium, gadolinium or neodymium; and polybutadiene rubber with a vinyl content of 0 to 75%; and combinations thereof; polybutadiene rubber with a high trans-1,4-unit content (>75%) or SBR containing, for example, between 5 and 45 wt % styrene and having a high trans-1,4-polybutadiene content (>75%) in the polybutadiene fraction of the copolymer (each type of polymer, SBR or BR, may be obtained with one or more initiator compounds comprising earth alkaline metal compounds, such as described in U.S. Pat. Nos. 6,693,160; 6,627,715; 6,489,415; 6,103,842; 5,753,579; 5,086,136; and 3,629,213, each of which is hereby incorporated herein by reference in its entirety; or by using catalysts based on cobalt, such as described in U.S. Pat. Nos. 6,310,152; 5,834,573; 5,753,761; 5,448,002 and 5,089,574 and U.S. Patent Application Publication No. 2003/0065114, each of which is hereby incorporated herein by reference in its entirety; or by using catalysts based on vanadium, such as described in EP 1 367 069; JP 11301794 and U.S. Pat. No. 3,951,936, each of which is hereby incorporated herein by reference in its entirety; or by using catalysts based on neodymium, such as described in EP 0 964 008, EP 0 924 214 and U.S. Pat. Nos. 6,184,168; 6,018,007; 4,931,376; 5,134,199 and 4,689,368, each of which is hereby incorporated herein by reference in its entirety).

The composition of the invention may also be used for producing high impact polystyrene (HIPS) and butadiene-modified acrylonitrile-butadiene-styrene copolymer (ABS) (see, for example, WO 2009/148932, incorporated herein by reference).

DEFINITIONS

Unless specifically indicated otherwise, the expression "polymer" as used herein is intended to encompass both unmodified polymer and modified (i.e. chain end-modified and backbone-modified) polymer.

Alkyl groups as defined herein, whether as such or in association with other groups, such as alkylaryl, include both straight chain alkyl groups, such as methyl (Me), ethyl (Et), n-propyl (Pr), n-butyl (Bu), n-pentyl, n-hexyl, etc., branched alkyl groups, such as isopropyl, tert-butyl, etc., and cyclic alkyl groups, such as cyclohexyl. Propyl encompasses n-propyl and isopropyl. Butyl encompasses n-butyl, sec-butyl, isobutyl and tert-butyl.

Aryl groups as defined herein include phenyl, biphenyl and other benzenoid compounds. Aryl groups preferably contain only one aromatic ring and most preferably contain a $C_6$ aromatic ring.

Alkylaryl groups as defined herein refer to a combination of one or more aryl groups bound to one or more alkyl groups, for example in the form of alkyl-aryl, aryl-alkyl, alkyl-aryl-alkyl and aryl-alkyl-aryl. Alkylaryl groups preferably contain only one aromatic ring and most preferably contain a $C_6$ aromatic ring.

The expression "independently selected from [list of chemical groups]" (emphasis added) in connection with the definition of plural chemical residues is intended to mean that each residue can be selected independently from the list of chemical groups. For instance, in a compound $SiR_4$, wherein each R is "independently selected from methyl, ethyl, propyl and butyl", all four groups may be either identical (such as in tetramethyl silane, $Si(Me)_4$) or fully or in part different (such as in trimethyl(propyl) silane).

Room temperature (RT or rt) refers to a temperature of 20° C.

Other abbreviations: DMPS=dimethylphenylsilyl, TBS=tert-butyldimethylsilyl, TEA=triethylamine, THF=tetrahydrofuran, DCM=dichloromethane, MTBE=tert-butylmethylether.

EXAMPLES

The following examples are provided in order to further illustrate the invention and are not to be construed as limiting.

The molecular weight analyses were carried out by SEC/RI using a HEWLETT PACKARD HP 1100. The eluent THF was degassed on line. The solvent flow rate was 1.0 ml/min. 100 μL of polymer solution were injected per analysis. The analyses were carried out at 40° C. The molecular weights were initially calculated based on a polystyrene calibration and given in the tables as polystyrene. The real molecular weights (SSBR molecular weights) were determined dividing by a factor derived from an earlier comparison between molecular weights from SEC/RI and SEC/MALLS. The value of the factor depends on the polymer composition (styrene and butadiene content). A factor of 1.52 was used for SSBR with 21% and 25% styrene. Mp (as SSBR) was used for the calculation of TMEDA molar ratios.

NMR spectroscopy was performed on a BRUKER Avance 400 in a 5 mm BBO probe. Solvents, frequencies and temperature is given in the characterization data.

FTIR-spectroscopy measured in attenuated total reflection was used to determine the vinyl content and styrene content.

The glass transition temperature was determined using the DSC Q2000 under the following conditions:
Weight: ca. 10-12 mg
Sample container: Alu/S
Temperature range: (−140 . . . 80)° C.
Heating rate: 20 K/min respectively 5 K/min
Cooling rate: free cooling
Purge gas: 20 ml Ar/min
Cooling agent: liquid nitrogen Each sample was measured at least once. The measurements contain two heating runs. The second heating run was used to determine the glass transition temperature.

Measurements of non-vulcanized rheological properties according to ASTM D 5289-95 were made using a rotor-less shear rheometer (MDR 2000 E) to characterize cure characteristics. Test pieces were vulcanized by t95 at 160° C., especially for hardness and rebound resilience tests the specimen were vulcanized by t95+5 min at 160° C. Tensile strength, elongation at break and moduli at 100% and 300% of deformation were measured according to ASTM D 412 on a Zwick Z010. DIN abrasion was measured according to DIN 53516 (1987-06-01). Hardness Shore A (ASTM D 2240) and Rebound resilience (ISO 4662) were measured at 0° C., RT and 60° C. Dynamic properties as tan δ at 0° C. and 60° C. were measured using dynamic spectrometer Eplexor 150N/500N manufactured by Gabo Qualimeter Testanlagen GmbH (Germany) applying a tension dynamic strain of −2% at a frequency of 2 Hz. Heat build up was measured according to ASTM D 623, method A, on a Doli 'Goodrich'-Flexometer.

Preparation and Characterization of Modifiers and Intermediates 1-(4-Bromophenyl)-1-phenylethene (1)

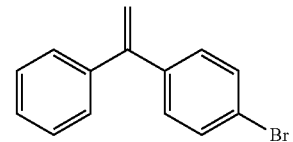

1

Preparation of Grignard-solution by dropwise addition of bromobenzene (8.68 g, 55.3 mmol, 1.1 equiv) to activated magnesium turnings (1.59 g, 65.3 mmol, 1.3 equiv.) in $Et_2O$ (80 ml). The dark reaction mixture was stirred at reflux temperature for 1.5 h and at rt for 16 h.

a) A solution of bromoacetophenon (10.0 g, 50.2 mmol, 1.0 equiv.) in $Et_2O$ (20 ml) was added at rt dropwise. Afterwards the reaction mixture was refluxed for 3.5 h. At rt water (100 ml) was added slowly followed by dil. HCl aq. (1 M, 50 ml). The phases were separated and the organic phase was washed with water (3×50 ml). The organic layer was dried over magnesium sulfate, the drying agent was filtered off and the solvent was removed under reduced pressure. The crude yellow oil (16.1 g) was used directly without further purification.

b) Crude alcohol was dissolved in toluene (150 ml). p-TosOH hydrate (400 mg) was added and the reaction mixture was refluxed with a Dean Stark trap for 3 h. At rt the reaction mixture was washed with water (30 ml) and the organic layer was dried over sodium sulfate, the drying agent was filtered off and the solvent was removed under reduced pressure. Distillation in vacuo furnished the title compound 1 (10.2 g, 39.4 mmol, 78%) as yellowish oil (see C. A. van Walree, V. E. M. Kaats-Richters, S. J. Veen, B. Wieczorek, J. H. van der Wiel, B. C. van der Wiel, *Eur. J. Org. Chem.* 2004, 3046-3056).

$C_{14}H_{11}Br$, $M_w$=259.15 g $mol^{-1}$ bp=150-156° C. (1.6 mbar).

$^1$H NMR (400 MHz, 20° C., $CDCl_3$): δ=7.45-7.43 (m, 2H), 7.34-7.29 (m, 5H), 7.23-7.19 (m, 2H), 5.46 (d, J=1.0 Hz, 1H), 5.44 (d, J=1.0 Hz, 1H) ppm.

$^{13}$C NMR (100 MHz, 20° C., $CDCl_3$): δ=148.99 (C), 140.90 (C), 140.39 (C), 131.29 (2CH), 129.88 (2CH), 128.26 (2CH), 128.17 (2CH), 127.93 (CH), 121.77 (C), 114.73 ($CH_2$) ppm.

GC-MS (EI, 70 eV): m/z (%)=258 (M$^+$, 56), 178 (M$^+$, 100), 89 (21), 51 (8).

(Diethylamino)(chloro)dimethylsilane (2a)

2a

A solution of dichlorodimethylsilane (5.00 g, 38.7 mmol, 1.0 equiv.) and triethylamine (4.31 g, 42.6 mmol, 1.1 equiv.) in anhydrous THF (5 ml) was stirred at rt. A solution of diethyl amine (2.83 g, 38.7 mmol, 1.0 equiv.) in THF (3 ml) was added dropwise (voluminous precipitation occurred). The reaction mixture was stirred at rt for 16 h. Filtration and removal of the solvent furnished a residue which was purified by vacuum distillation. Chloroaminosilane 2a (4.58 g, 27.6 mmol, 71%) was received as colorless liquid.

$C_6H_{16}ClNSi$, $M_w$=165.74 g mol$^{-1}$
bp=77-80° C. (30 mbar).
$^1$H NMR (400 MHz, 20° C., $C_6D_6$): δ=2.69 (q, J=7.1 Hz, 4H), 0.89 (t, J=6.9 Hz, 6H), 0.31 (s, 6H) ppm.
$^{13}$C NMR (100 MHz, 20° C., $C_6D_6$): δ=40.07 (2CH$_2$), 15.38 (2CH$_3$), 1.94 (2CH$_3$) ppm.

(Morpholino)(chloro)dimethylsilane (2b)

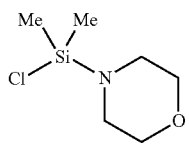

2b

A solution of dichlorodimethylsilane (15.0 g, 116 mmol, 1.0 equiv.) and triethylamine (12.3 g, 122 mmol, 1.1 equiv.) in anhydrous THF (30 ml) was stirred at rt. A solution of morpholine (10.1 g, 116 mmol, 1.0 equiv.) in THF (15 ml) was added dropwise (voluminous precipitation occurred). The reaction mixture was stirred at rt for 16 h. Filtration and removal of the solvent furnished a residue which was purified by vacuum distillation. Chloroaminosilane 2b (8.8 g, 49 mmol, 42%) was received as colorless liquid.

$C_6H_{14}ClNSi$, $M_w$=179.72 g mol$^{-1}$
bp=53-55° C. (4 mbar).
$^1$H NMR (400 MHz, 20° C., $C_6D_6$): δ=3.39-3.37 (m, 4H), 2.63-2.61 (m, 4H), 0.19 (s, 6H) ppm.
$^{13}$C NMR (100 MHz, 20° C., $C_6D_6$): δ=67.85 (2CH$_2$), 45.24 (2CH$_2$), 0.91 (2CH$_3$) ppm.

(tert-Butyldimethylsiloxy)(chloro)dimethylsilane (2c)

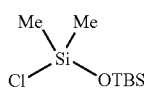

2c

A solution of TBSOH (10.3 g, 77.5 mmol, 1.0 equiv.) in THF (50 ml) was treated with TEA (8.61 g, 85.3 mmol, 1.1 equiv.) at rt. Then dichlorodimethylsilane (10.0 g, 77.5 mmol, 1.0 equiv.) was added dropwise and the reaction mixture was stirred at rt for 16 h. Filtration and removal of the solvent furnished a residue which was purified by vacuum distillation. Chlorosilane 2c (11.5 g, 51.1 mmol, 66%) was received as colorless liquid.

$C_8H_{26}OClSi_2$, $M_w$=224.88 g mol$^{-1}$
bp=76-77° C. (40 mbar).
$^1$H NMR (400 MHz, 20° C., $C_6D_6$): δ=0.90 (s, 9H), 0.29 (s, 6H), 0.07 (s, 6H) ppm.
$^{13}$C NMR (100 MHz, 20° C., $C_6D_6$): δ=25.67 (3CH$_3$), 18.12 (C), 4.08 (2CH$_3$), −3.09 (2CH$_3$) ppm.
GC-MS (EI, 70 eV): m/z (%)=236 (M$^+$, 0.1), 221 (M$^+$-CH$_3$, 1), 179 (M$^+$-C$_4$H$_9$, 100), 137 (9), 93 (Me$_2$SiCl$^+$, 8).

1-(Chlorodimethylsilyl)-4-methylpiperazine (2d)

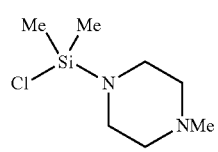

2d

A solution of dichlorodimethylsilane (10.0 g, 77.5 mmol, 1.0 equiv.) in anhydrous MTBE (25 ml) was stirred at rt. Independently, a solution of methylpiperazine (7.76 g, 77.5 mmol, 1.0 equiv.) in cyclohexane (20 ml) was treated dropwise with nBuLi solution (24.6 g, 77.5 mmol, 1.0 equiv.). After some minutes this suspension was added slowly to the silane solution in MTBE. The reaction mixture was diluted with cyclohexane (50 ml) and it was stirred at rt for 17 h. Filtration and removal of the solvent furnished a residue which was purified by vacuum distillation. Chloroaminosilane 2d (8.87 g, 46.0 mmol, 59%) was received as colorless liquid.

$C_7H_{17}ClN_2Si$, $M_w$=192.76 g mol$^{-1}$
bp=92-97° C. (25 mbar).
$^1$H NMR (400 MHz, 20° C., $C_6D_6$): δ=2.84 (t, J=4.9 Hz, 4H), 2.09 (t, J=4.6 Hz, 4H), 2.10 (s, 3H), 0.26 (s, 6H) ppm.
$^{13}$C NMR (100 MHz, 20° C., $C_6D_6$): δ=56.32 (2CH$_2$), 46.73 (CH$_3$), 45.12 (2CH$_2$), 1.26 (2 CH$_3$) ppm.
GC-MS (EI, 70 eV): m/z (%)=192 (M$^+$, 100), 177 (M$^+$-CH$_3$, 17), 157 (45), 121 (63), 93 (Me$_2$SiCl$^+$, 64).

(Dibutylamino)(chloro)dimethylsilane (2e)

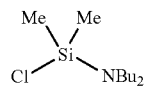

2e

A solution of dichlorodimethylsilane (5.00 g, 38.7 mmol, 1.0 equiv.) and triethylamine (4.31 g, 42.6 mmol, 1.1 equiv.) in anhydrous THF (10 ml) was stirred at rt. A solution of dibutyl amine (5.00 g, 38.7 mmol, 1.0 equiv.) in THF (5 ml) was added dropwise (voluminous precipitation occurred). The reaction mixture was stirred at rt for 16 h. Filtration and removal of the solvent furnished a residue which was purified by vacuum distillation. Chloroaminosilane 2e (6.76 g, 30.5 mmol, 79%) was received as colorless liquid.

C$_{10}$H$_{24}$ClNSi, M$_w$=221.85 g mol$^{-1}$ bp=93-95° C. (20 mbar).

$^1$H NMR (400 MHz, 20° C., C$_6$D$_6$): δ=2.73-2.62 (m, 4H), 1.41-1.33 (m, 4H), 1.15 (sext, J=7.4 Hz, 4H), 0.85 (t, J=7.3 Hz, 6H), 0.36 (s, 6H) ppm.

$^{13}$C NMR (100 MHz, 20° C., C$_6$D$_6$): δ=46.12 (2CH$_2$), 32.04 (2CH$_2$), 20.54 (2CH$_2$), 14.24 (2 CH$_3$), 2.18 (2CH$_3$) ppm.

GC-MS (EI, 70 eV): m/z (%)=221 (M$^+$, 5), 178 (100), 136 (66), 93 (Me$_2$SiCl$^+$, 26).

(N-Piperidino)(chloro)dimethylsilane (2f)

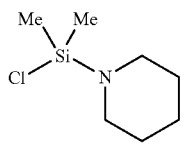

2f

A solution of dichlorodimethylsilane (5.00 g, 38.7 mmol, 1.0 equiv.) and triethylamine (4.31 g, 42.6 mmol, 1.1 equiv.) in anhydrous THF (10 ml) was stirred at rt. A solution of piperidine (3.30 g, 38.7 mmol, 1.0 equiv.) in THF (10 ml) was added dropwise (voluminous precipitation occurred). The reaction mixture was stirred at rt for 18 h. Filtration and removal of the solvent furnished a residue which was purified by vacuum distillation. Chloroaminosilane 2f (2.26 g, 12.7 mmol, 33%) was received as colorless liquid.

C$_7$H$_{16}$ClNSi, M$_w$=177.75 g mol$^{-1}$ bp=105-107° C. (20 mbar).

$^1$H NMR (400 MHz, 20° C., C$_6$D$_6$): δ=2.74 (t, J=5.2 Hz, 4H), 1.41-1.36 (m, 2H), 1.32-1.26 (m, 4H), 0.29 (s, 6H) ppm.

$^{13}$C NMR (100 MHz, 20° C., C$_6$D$_6$): δ=46.17 (2CH$_2$), 27.37 (2CH$_2$), 25.46 (CH$_2$), 1.40 (2CH$_3$) ppm.

GC-MS (EI, 70 eV): m/z (%)=177 (M$^+$, 29), 176 (M$^+$-H, 100), 162 (M$^+$-CH$_3$, 17), 142 (17), 120 (11), 93 (Me$_2$SiCl$^+$, 26).

(Diethylamino)(tert-butyldimethylsiloxy)(chloro)methylsilane (2g)

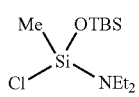

2g

A solution of trichloromethylsilane (5.00 g, 33.4 mmol, 1.0 equiv.) and triethylamine (6.77 g, 66.9 mmol, 2.0 equiv.) in anhydrous THF (100 ml) was stirred at rt. TBSOH (4.42 g, 33.4 mmol, 1.0 equiv.) was added and the mixture was stirred for 1.5 h. Then diethylamine (2.45 g, 33.4 mmol, 1.0 equiv.) was added slowly and voluminous precipitation occurred. The reaction mixture was stirred at rt for 3 d. Filtration and removal of the solvent furnished a residue which was purified by vacuum distillation. Chloroaminosilane 2g (7.64 g, 27.1 mmol, 81%) was received as colorless liquid.

C$_{11}$H$_{28}$ClNOSi$_2$, M$_w$=281.97 g mol$^{-1}$ bp=77-79° C. (5 mbar).

$^1$H NMR (400 MHz, 20° C., C$_6$D$_6$): δ=2.80 (q, J=7.2 Hz, 4H), 0.96 (t, J=7.1 Hz, 6H), 0.94 (s, 9H), 0.37 (s, 3H), 0.14 (s, 3H), 0.13 (s, 3H) ppm.

$^{13}$C NMR (100 MHz, 20° C., C$_6$D$_6$): δ=39.15 (2CH$_2$), 25.74 (3CH$_3$), 18.28 (C), 15.34 (2CH$_3$), 1.74 (CH$_3$), −3.13 (2CH$_3$) ppm.

GC-MS (EI, 70 eV): m/z (%)=177 (M$^+$, 29), 176 (M$^+$-H, 100), 162 (M$^+$-CH$_3$, 17), 142 (17), 120 (11), 93 (Me$_2$SiCl$^+$, 26).

N,N-Diethyl-1,1-dimethyl-1-[4-(1-phenylvinyl)phenyl]silanamine (I-1a)

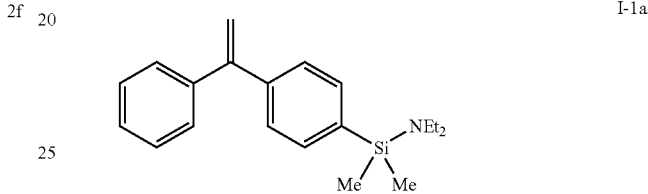

I-1a nBuLi-solution (3.25 g, 10.1 mmol, 1.05 equiv.) in cyclohexane was added to a solution of bromoarene 1 (2.50 g, 9.65 mmol, 1.00 equiv.) in THF (45 ml) at −80° C. After 30 min at this temperature the mixture was allowed to warm to rt. The solution was stirred for 10 min at rt. At −80° C. chloroaminosilane 2a (2.20 g, 14.5 mmol, 1.50 equiv.) was added and subsequently the mixture was allowed to stir 30 min at rt. As a result a color change to bright yellow occurred to indicate full conversion. Then diethylamine (318 mg, 4.34 mmol, 0.45 equiv.) was added and the solvent was reduced. Addition of cyclohexane (50 ml) and filtration followed by removal of the solvent furnished an oily residue which was distilled in vacuo. I-1a (1.70 g, 5.49 mmol, 57%) was received as colorless oil.

C$_{20}$H$_{27}$NSi, M$_w$=309.53 g mol$^{-1}$ bp=160-165° C. (6.6×10$^{-3}$ mbar).

$^1$H NMR (400 MHz, 20° C., C$_6$D$_6$): δ=7.56-7.54 (m, 2H), 7.42-7.40 (m, 2H), 7.35-7.32 (m, 2H), 7.11-7.09 (m, 3H), 5.44 (d, J=1.4 Hz, 1H), 5.40 (d, J=1.3 Hz, 1H), 2.79 (q, J=7.0 Hz, 4H), 0.99 (t, J=7.0 Hz, 6H), 0.32 (s, 6H) ppm.

$^{13}$C NMR (100 MHz, 20° C., C$_6$D$_6$): δ=150.82 (C), 142.47 (C), 141.99 (C), 140.23 (C), 134.17 (2CH), 128.72 (2CH), 128.49 (2CH), 128.03 (2CH), 127.95 (CH), 114.39 (CH$_2$) 40.47 (2CH$_2$), 16.04 (2CH$_3$), −1.01 (2CH$_3$) ppm.

GC-MS (EI, 70 eV): m/z (%)=309 (M$^+$, 9), 294 (M$^+$-CH$_3$, 95), 237 (M$^+$-NEt$_2$, 100), 178 (7), 147 (7), 103 (4).

4-{Dimethyl[4-(1-phenylvinyl)phenyl]silyl}morpholine (I-1b)

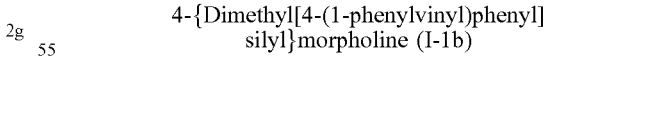

I-1b nBuLi-solution (7.72 g, 24.3 mmol, 1.05 equiv.) in cyclohexane was added to a solution of bromoarene 1 (6.00 g, 23.2 mmol, 1.00 equiv.) in THF (70 ml) at −80° C. After 30 min at this temperature the mixture was allowed to warm to rt. The solution was stirred for 10 min at rt. At −80° C. chloroaminosilane 2b (5.83 g, 32.4 mmol, 1.40 equiv.) was added and subsequently the mixture was allowed to stir 30 min at rt. As a result a color change to bright yellow occurred to indicate full conversion. Then morpholine (1.51 g, 17.4 mmol, 0.75 equiv.) was added and the solvent was reduced. Addition of cyclohexane (50 ml) and filtration followed by removal of the solvent furnished an oily residue which was distilled in vacuo. I-1b (5.78 g, 17.9 mmol, 77%) was received as yellow oil.

$C_{20}H_{25}NOSi$, $M_w$=323.51 g mol$^{-1}$
bp=163-170° C. (6×10$^{-3}$ mbar).
$^1$H NMR (400 MHz, 20° C., $C_6D_6$): δ=7.49-7.47 (m, 2H), 7.41-7.39 (m, 2H), 7.35-7.32 (m, 2H), 7.12-7.10 (m, 3H), 5.45 (d, J=1.3 Hz, 1H), 5.40 (d, J=1.3 Hz, 1H), 3.45-3.42 (m, 4H), 2.71-2.69 (m, 4H), 0.21 (s, 6H) ppm.
$^{13}$C NMR (100 MHz, 20° C., $C_6D_6$): δ=150.71 (C), 142.80 (C), 141.87 (C), 138.62 (C), 134.18 (2CH), 128.68 (2CH), 128.52 (2CH), 128.09 (2CH), 128.02 (CH), 114.56 ($CH_2$) 68.56 (2$CH_2$), 46.05 (2$CH_2$), −2.31 (2$CH_3$) ppm.
GC-MS (EI, 70 eV): m/z (%)=323 (M$^+$, 65), 308 (M$^+$-$CH_3$, 41), 278 (7), 237 (M$^+$-N$C_4H_8$O, 100), 206 (7), 178 (13), 145 (3), 118 (8).

1-(tert-Butyldimethylsiloxy)-1,1-dimethyl-1-[4-(1-phenylvinyl)phenyl]silane (I-1c)

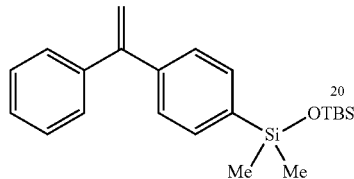

I-1c nBuLi-solution (5.78 g, 18.2 mmol, 1.05 equiv.) in cyclohexane was added to a solution of bromoarene 1 (4.50 g, 17.4 mmol, 1.00 equiv.) in THF (50 ml) at −80° C. After 30 min at this temperature the mixture was allowed to warm to rt. The solution was stirred for 10 min at rt. At −80° C. chlorosiloxysilane 2c (5.47 g, 24.3 mmol, 1.40 equiv.) was added and subsequently the mixture was allowed to stir 30 min at rt. As a result a color change to bright yellow occurred to indicate full conversion. Then TBSOH (1.61 g, 12.2 mmol, 0.70 equiv.) was added and the solvent was reduced. Addition of cyclohexane (50 ml) and filtration followed by removal of the solvent furnished an oily residue which was distilled in vacuo. I-1c (5.49 g, 14.9 mmol, 86%) was received as yellow oil.

$C_{22}H_{32}OSi_2$, $M_w$=368.67 g mol$^{-1}$
bp=145-150° C. (6.8×10$^{-3}$ mbar).
$^1$H NMR (400 MHz, 20° C., $C_6D_6$): δ=7.57-7.55 (m, 2H), 7.40-7.38 (m, 2H), 7.33-7.30 (m, 2H), 7.11-7.08 (m, 3H), 5.42 (d, J=1.3 Hz, 1H), 5.39 (d, J=1.3 Hz, 1H), 0.94 (s, 9H), 0.34 (s, 6H), 0.07 (s, 6H) ppm.
$^{13}$C NMR (100 MHz, 20° C., $C_6D_6$): δ=150.72 (C), 142.91 (C), 141.92 (C), 139.65 (C), 133.36 (2CH), 128.68 (2CH), 128.51 (2CH), 128.10 (2CH), 128.00 (CH), 114.55 ($CH_2$) 25.93 (3$CH_3$), 18.32 (C), 1.11 (2$CH_3$), −2.68 (2$CH_3$) ppm.
GC-MS (EI, 70 eV): m/z (%)=368 (M$^+$, 1), 353 (M$^+$-$CH_3$, 2), 311 (M$^+$-$C_4H_9$, 100), 221 (49), 193 (18), 155 (9), 103 (8), 73 (12).

1-{Dimethyl[4-(1-phenylvinyl)phenyl]silyl}-4-methylpiperazine (I-1d)

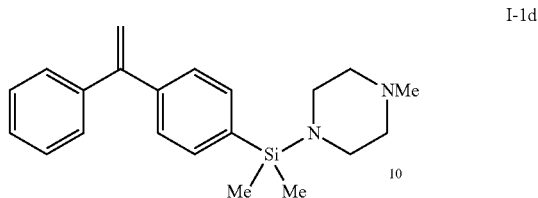 [SMILES: C=C(c1ccccc1)c1ccc([Si](C)(C)N2CCN(C)CC2)cc1]

I-1d nBuLi-solution (2.60 mg, 0.810 mmol, 1.05 equiv.) in cyclohexane was added to a solution of bromoarene 1 (200 mg, 0.772 mmol, 1.00 equiv.) in THF (3 ml) at −80° C. After 30 min at this temperature the mixture was allowed to warm to rt. The solution was stirred for 10 min at rt. At −80° C. chloroaminosilane 2d (179 mg, 0.926 mmol, 1.20 equiv.) was added and subsequently the mixture was allowed to stir 30 min at rt. As a result a color change to bright yellow occurred to indicate full conversion. GC/MS-analysis indicated the conversion of bromoarene 1 into the title compound I-1d. Purity: 74%.

$C_{29}H_{28}N_2Si$, $M_w$=336.55 g mol$^{-1}$
GC-MS (EI, 70 eV): m/z (%)=336 (M$^+$, 63), 321 (M$^+$-$CH_3$, 6), 294 (8), 266 (19), 237 (M$^+$-$N_2C_5H_{11}$, 100), 156 (17), 99 (9).

N,N-Dibutyl-1,1-dimethyl-1-[4-(1-phenylvinyl)phenyl]silanamine (I-1e)

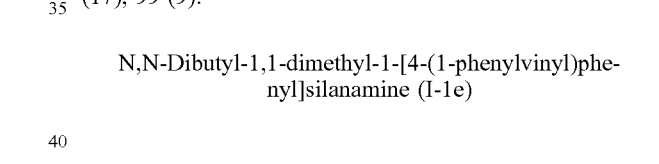

I-1e nBuLi-solution (260 mg, 0.810 mmol, 1.05 equiv.) in cyclohexane was added to a solution of bromoarene 1 (200 mg, 0.772 mmol, 1.00 equiv.) in THF (3 ml) at −80° C. After 30 min at this temperature the mixture was allowed to warm to rt. The solution was stirred for 10 min at rt. At −80° C. chloroaminosilane 2e (240 mg, 1.08 mmol, 1.40 equiv.) was added and subsequently the mixture was allowed to stir 30 min at rt. As a result a color change to bright yellow occurred to indicate full conversion. Then dibutylamine (50 mg, 0.39 mmol, 0.50 equiv.) and cyclohexane (5 ml) were added. GC/MS-analysis indicated the conversion of bromoarene 1 into the title compound I-1e. Purity: 62%.

$C_{24}H_{35}NSi$, $M_w$=365.63 g mol$^{-1}$
GC-MS (EI, 70 eV): m/z (%)=365 (M$^+$, 4), 350 (M$^+$-$CH_3$, 3), 322 (M$^+$-$C_3H_7$, 100), 280 (4), 237 (M$^+$-N$C_8H_{18}$, 100), 178 (7), 118 (12).

N,N-Diethyl-1-[(tert-butyldimethyl)siloxy]-1-methyl-1-[4-(1-phenylvinyl)phenyl]-silanamine (I-1f)

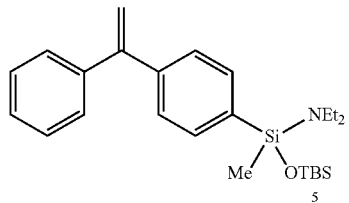

I-1f nBuLi-solution (2.60 g, 8.10 mmol, 1.05 equiv.) in cyclohexane was added to a solution of bromoarene 1 (2.00 g, 7.72 mmol, 1.00 equiv.) in THF (25 ml) at −80° C. After 30 min at this temperature the mixture was allowed to warm to rt. The solution was stirred for 10 min at rt. At −80° C. chloroaminosilane 2 g (3.05 g, 10.8 mmol, 1.40 equiv.) was added and subsequently the mixture was allowed to stir 30 min at rt. As a result a color change to bright yellow occurred to indicate full conversion. Then diethylamine (452 mg, 6.18 mmol, 0.80 equiv.) was added and the solvent was reduced. Addition of cyclohexane (25 ml) and filtration followed by removal of all volatile materials (@ $4 \times 10^{-3}$ mbar and 90° C.) an oily residue I-1f (2.30 g, 5.40 mmol, 70%) was received as colorless oil in 90% purity.

$C_{25}H_{39}NOSi_2$, $M_w$=425.77 g mol$^{-1}$ $^1$H NMR (400 MHz, 20° C., $C_6D_6$): δ=7.73-7.71 (m, 2H), 7.43-7.41 (m, 2H), 7.33-7.31 (m, 2H), 7.11-7.08 (m, 3H), 5.43 (d, J=1.2 Hz, 1H), 5.37 (d, J=1.2 Hz, 1H), 2.88 (dq, J=14.0 Hz, J=7.0 Hz, 2H), 2.84 (dq, J=14.1 Hz, J=6.9 Hz, 2H), 1.01 (s, 9H), 0.97 (t, J=7.0 Hz, 6H), 0.36 (s, 3H), 0.15 (s, 6H) ppm.

$^{13}$C NMR (100 MHz, 20° C., $C_6D_6$): δ=150.78 (C), 142.76 (C), 142.00 (C), 138.58 (C), 134.50 (2CH), 128.73 (2CH), 128.49 (2CH), 127.97 (2CH), 127.92 (CH), 114.53 ($CH_2$) 39.85 (2$CH_2$), 26.06 (3$CH_3$), 18.54 (C), 15.90 (2$CH_3$), −0.75 ($CH_3$), −2.61 ($CH_3$), −2.62 ($CH_3$) ppm.

GC-MS (EI, 70 eV): m/z (%)=425 (M$^+$, 7), 410 (M$^+$-$CH_3$, 100), 368 (15), 311 (23), 281 (3), 221 (21), 193 (46), 147 (24), 103 (11), 73 (13).

1-Ally-4-(1-phenylvinyl)benzene (3)

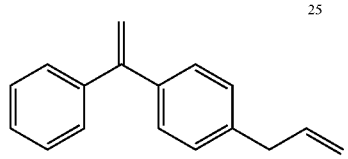

3

Allyltributyltin (1.25 g, 3.78 mmol, 1.40 equiv.) was added to a solution of Br-DPE 1 (700 mg, 2.70 mmol, 1.00 equiv.), Pd(PPh$_3$)$_4$ (53 mg, 0.05 mmol, 1.7 mol %), PPh$_3$ (14 mg, 0.05 mmol, 2 mol %) and LiCl (457 mg, 10.8 mmol, 4.00 equiv.) in anhyd. DMF (7 ml) at rt. The mixture was stirred under Argon at 90° C. for 3 h. The brown reaction mixture was cooled to rt, then cyclohexane (25 ml) and sat. aqueous solution of NaHCO$_3$ (25 ml) was added. The layers were separated. The aqueous phase was extracted with EA (20 ml) and the combined organic phases were washed with water (3×15 ml). The organic phase was dried over Na$_2$SO$_4$, the drying agent was filtered off and the solvent was removed under reduced pressure. The crude yellow oil was purified by column chromatography (SiO$_2$, CH/EA=100:0 to 95:5). Arene 3 (570 mg, 2.60 mmol, 96%) was received as colorless oil.

$C_{17}H_{16}$, $M_w$=220.31 g mol$^{-1}$ $R_f$=0.65 (Cyclohexane/EA=10:1).

$^1$H NMR (400 MHz, 20° C., CDCl$_3$): δ=7.34-7.30 (m, 5H), 7.28-7.26 (m, 2H), 7.17-7.15 (m, 2H), 5.99 (ddt, J=16.9 Hz, J=10.1 Hz, J=6.8 Hz, 1H), 5.44 (d, J=1.2 Hz, 1H), 5.43 (d, J=1.2 Hz, 1H), 5.10 (ddt, J=16.9 Hz, J=1.7 Hz, J=1.6 Hz, 1H), 5.09 (dtd, J=10.0 Hz, J=1.6 Hz, J=1.2 Hz, 1H), 3.40 (d, J=6.7 Hz, 1H) ppm.

$^{13}$C NMR (100 MHz, 20° C., CDCl$_3$): δ=149.79 (C), 141.57 (C), 139.64 (C), 139.27 (C), 137.29 (CH), 128.34 (2CH), 128.30 (2CH), 128.27 (2CH), 128.11 (2CH), 127.65 (CH), 115.92 ($CH_2$), 113.88 ($CH_2$), 39.93 ($CH_2$) ppm.

FT-IR (ATR) 1/λ, =3078 (w), 3052 (w), 3024 (w), 2924 (m), 2850 (w), 1802 (w), 1609 (w), 1492 (m), 1444(m), 1327 (w), 992 (m), 895 (m), 776 (s), 699 (s) cm$^{-1}$.

GC-MS (EI, 70 eV): m/z (%)=220 (M$^+$, 100), 205 (31), 178 (49), 141 (14), 117 (50), 103 (73), 91 (15), 77 (23).

Chlorodimethyl{3-[4-(1-phenylvinyl)phenyl]propyl}silane (4)

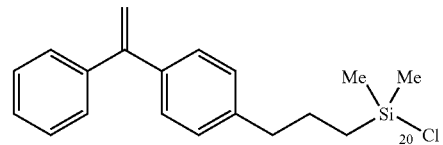

4

A solution of Allyl-DPE 3 (2.0 g, 2.27 mmol, 25 wt % in cyclohexane) was diluted with THF (1.0 ml). After addition of chlorodimethylsilane (225 mg, 2.38 mmol, 1.05 equiv.) a solution of Karstedt's catalyst in xylene (2.1-2.4 wt % Pt, 20 mg, 2.3 μmol, 0.1 mol %) was added and the reaction mixture was stirred at rt for 3 h. A GC/MS-aliquot was taken and showed the right molecular mass. The title compound was directly used to prepare silaneamines.

$C_{19}H_{23}ClSi$, $M_w$=314.93 g mol$^{-1}$

GC-MS (EI, 70 eV): m/z (%)=314 (M$^+$, 63), 286 (9), 193 (100), 165 (9), 141 (1), 115 (10), 93 (Me$_2$SiCl$^+$, 92), 65 (9).

N,N-Diethyldimethyl{3-[4-(1-phenylvinyl)phenyl]propyl}silanamine (I-2a)

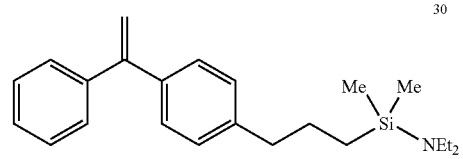

I-2a

A solution of Allyl-DPE 3 (2.0 g, 2.27 mmol, 25 wt % in cyclohexane) was diluted with THF (1.0 ml). After addition of chlorodimethylsilane (225 mg, 2.38 mmol, 1.05 equiv.) a solution of Karstedt's catalyst in xylene (2.1-2.4 wt % Pt, 20 mg, 2.3 µmol, 0.1 mol %) was added and the reaction mixture was stirred at rt for 4 h. Then diethylamine (498 mg, 6.81 mmol, 3.0 equiv.) was added and the reaction mixture was stirred for a further 16 h. After filtration and removal of all volatile materials in vacuo (4×10⁻³ mbar, 90° C.) silanamin I-2a (577 mg, 1.64 mmol, 72%) was received as a brownish oil. Purity: 95% (NMR).

$C_{23}H_{33}NSi$, $M_w$=351.61 g mol⁻¹

¹H NMR (400 MHz, 20° C., $C_6D_6$): δ=7.36-7.32 (m, 4H), 7.14-7.06 (m, 5H), 5.41 (d, J=1.4 Hz, 1H), 5.36 (d, J=1.4 Hz, 1H), 2.71 (q, J=7.0 Hz, 4H), 2.57 (t, J=7.6 Hz, 2H), 1.69-1.61 (m, 2H), 0.93 (t, J=7.6 Hz, 6H), 0.61-0.56 (m, 2H), 0.06 (s, 6H) ppm.

¹³C NMR (100 MHz, 20° C., $C_6D_6$): δ=150.66 (C), 142.69 (C), 142.25 (C), 139.48 (C), 128.73 (4CH), 128.67 (2CH), 128.47 (2CH), 127.90 (CH), 113.73 ($CH_2$), 40.32 ($CH_2$), 40.05 ($CH_2$), 26.53 ($CH_2$), 17.19 ($CH_2$), 16.18 ($2CH_3$), −1.59 ($2CH_3$) ppm.

GC-MS (EI, 70 eV): m/z (%)=351 (M⁺, 23), 336 (M⁺-$CH_3$, 13), 279 (M⁺-$NC_2H_{10}$, 100), 250 (6), 220 (4), 175 (17), 130 (69), 102 (25), 59 (71).

N,N-Dibutyldimethyl{3-[4-(1-phenylvinyl)phenyl]propyl}silanamine (I-2b)

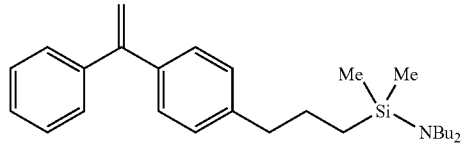

I-2b

A solution of Allyl-DPE 3 (2.0 g, 2.27 mmol, 25 wt % in cyclohexane) was diluted with THF (1.0 ml). After addition of chlorodimethylsilane (225 mg, 2.38 mmol, 1.05 equiv.) a solution of Karstedt's catalyst in xylene (2.1-2.4 wt % Pt, 20 mg, 2.3 µmol, 0.1 mol %) was added and the reaction mixture was stirred at rt for 4 h. Then dibutylamine (616 mg, 4.77 mmol, 2.0 equiv.) was added and the reaction mixture was stirred for a further 16 h. After filtration and removal of all volatile materials in vacuo (4×10⁻³ mbar, 90° C.) silanamin I-2b (734 mg, 1.80 mmol, 79%) was received as a brownish oil. Purity: about 95% (NMR).

$C_{27}H_{41}NSi$, $M_w$=407.71 g mol⁻¹

¹H NMR (400 MHz, 20° C., $C_6D_6$): δ=7.37-7.32 (m, 4H), 7.11-7.07 (m, 5H), 5.41 (d, J=1.4 Hz, 1H), 5.36 (d, J=1.4 Hz, 1H), 2.73-2.69 (m, 4H), 2.59 (t, J=7.6 Hz, 2H), 1.72-1.64 (m, 2H), 1.43-1.36 (m, 4H), 1.21 (sext, J=7.6 Hz, 4H), 0.90 (t, J=7.3 Hz, 6H), 0.66-0.61 (m, 2H), 0.10 (s, 6H) ppm.

¹³C NMR (100 MHz, 20° C., $C_6D_6$): δ=150.66 (C), 142.67 (C), 142.25 (C), 139.48 (C), 128.75 (2CH), 128.73 (2CH), 128.67 (2CH), 128.46 (2CH), 127.90 (CH), 113.73 ($CH_2$), 46.72 ($2CH_2$), 40.08 ($CH_2$), 32.96 ($2CH_2$), 26.59 ($CH_2$), 20.69 ($2CH_2$), 17.17 ($CH_2$), 14.42 ($2CH_3$), −1.48 ($2CH_3$) ppm.

GC-MS (EI, 70 eV): m/z (%)=407 (M⁺, 11), 364 (54), 279 (M⁻-$NBu_2$, 100), 220 (6), 175 (31), 135 (17), 86 (28), 59 (61).

4-<Dimethyl{3-[4-(1-phenylvinyl)phenyl]propyl}silyl>morpholine (I-2c)

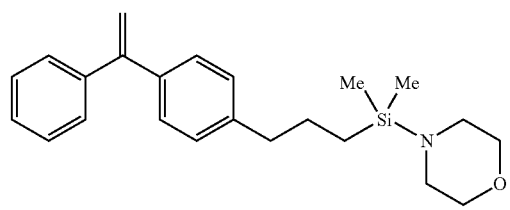

I-2c

A solution of Allyl-DPE 3 (2.0 g, 2.27 mmol, 25 wt % in cyclohexane) was diluted with THF (1.0 ml). After addition of chlorodimethylsilane (225 mg, 2.38 mmol, 1.05 equiv.) a solution of Karstedt's catalyst in xylene (2.1-2.4 wt % Pt, 20 mg, 2.3 µmol, 0.1 mol %) was added and the reaction mixture was stirred at rt for 4 h. Then morpholine (593 mg, 6.81 mmol, 3.0 equiv.) was added and the reaction mixture was stirred for a further 16 h. After filtration and removal of all volatile materials in vacuo (4×10⁻³ mbar, 90° C.) silanamin I-2c (458 mg, 1.25 mmol, 55%) was received as a brownish oil. Purity: 95% (NMR).

$C_{23}H_{31}NOSi$, $M_w$=365.59 g mol⁻¹

1H NMR (400 MHz, 20° C., $C_6D_6$): δ=7.37-7.33 (m, 4H), 7.13-7.06 (m, 5H), 5.42 (d, J=1.4 Hz, 1H), 5.37 (d, J=1.4 Hz, 1H), 3.44-3.42 (m, 4H), 2.62-2.60 (m, 4H), 2.55 (t, J=7.6 Hz, 2H), 1.61-1.54 (m, 2H), 0.51-0.47 (m, 2H), −0.06 (s, 6H) ppm.

¹³C NMR (100 MHz, 20° C., $C_6D_6$): δ=150.60 (C), 142.48 (C), 142.19 (C), 139.60 (C), 128.71 (4CH), 128.49 (2CH), 128.32 (2CH), 127.94 (CH), 113.82 ($CH_2$), 68.65 ($2CH_2$), 45.93 ($2CH_2$), 39.85 ($CH_2$), 26.25 ($CH_2$), 15.92 ($CH_2$), −2.81 ($2CH_3$) ppm.

GC-MS (EI, 70 eV): m/z (%)=365 (M⁺, 67), 350 (M⁺-$CH_3$, 7), 320 (1), 279 (19), 250 (28), 220 (3), 178 (15), 144 (69), 102 (100), 59 (88).

(tert-Butyldimethylsiloxy)N,N-diethylmethyl{3-[4-(1-phenylvinyl)phenyl]propyl}silanamine (I-2d)

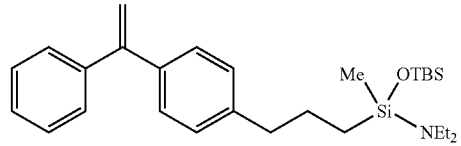

I-2d

A solution of Allyl-DPE 3 (2.0 g, 2.27 mmol, 25 wt % in cyclohexane) was diluted with THF (1.0 ml). After addition of dichloromethylsilane (264 mg, 2.29 mmol, 1.01 equiv.) a solution of Karstedt's catalyst in xylene (2.1-2.4 wt % Pt, 20 mg, 2.3 µmol, 0.1 mol %) was added and the reaction mixture was stirred at rt for 3 h. Then TBSOH (300 mg, 2.27 mmol, 1.0 equiv.) was added followed by TEA (230 mg, 2.27 mmol, 1.0 equiv.). The reaction mixture was stirred for 16 h at rt. Then diethylamine (498 mg, 6.81 mmol, 3.0 equiv.) was added and the reaction mixture was stirred for a further 4 h. After filtration and removal of all volatile materials in vacuo (4×10⁻³ mbar, 90° C.) silanamin 1-2d (1.24 g, 2.65 mmol, >100%) was received as a brownish oil.

Purity: about 80% (NMR) (approx. calculated yield: 0.99 g, 2.12 mmol, 93%).

$C_{28}H_{45}NOSi_2$, $M_w$=467.83 g mol⁻¹

¹H NMR (400 MHz, 20° C., $C_6D_6$): δ=7.36-7.31 (m, 4H), 7.13-7.08 (m, 5H), 5.40 (d, J=1.4 Hz, 1H), 5.36 (d, J=1.3 Hz, 1H), 2.79 (q, J=7.0 Hz, 4H), 2.59 (t, J=7.2 Hz, 2H), 1.77-1.69 (m, 2H), 0.97 (s, 9H), 0.97 (t, J=6.9 Hz, 6H), 0.70-0.65 (m, 2H), 0.11 (s, 3H), 0.09 (s, 6H) ppm.

¹³C NMR (100 MHz, 20° C., $C_6D_6$): δ=150.66 (C), 142.61 (C), 142.25 (C), 139.50 (C), 128.82 (4CH), 128.68 (2CH), 128.46 (2CH), 127.90 (CH), 113.72 ($CH_2$), 39.87 ($CH_2$), 39.69 (2$CH_2$), 26.32 ($CH_2$), 26.01 (3$CH_3$), 18.43 (C), 16.71 ($CH_2$), 16.06 (2$CH_3$), −1.83 ($CH_3$), −2.68 (2$CH_3$) ppm.

GC-MS (EI, 70 eV): m/z (%)=467 (M⁺, 44), 452 (M⁺-$CH_3$, 36), 438 (9), 410 (15), 395 (61), 353 (11), 295 (19), 246 (81), 207 (38), 133 (100), 58 (60).

Lithiated Precursors (After Reaction of I-1a, b, c, f with nBuLi and Quenched with Proton Source)

L-I-1a $C_{24}H_{37}NSi$, $M_w$=367.65 g mol⁻¹

GC-MS (EI, 70 eV): m/z (%)=367 (M⁺, 7), 352 (M⁺-$CH_3$, 100), 295 (47), 259 (3), 224 (11), 167 (11), 140 (5), 111 (11), 85 (17), 57 (41).

L-I-1b $C_{24}H_{35}NOSi$, $M_w$=381.62 g mol⁻¹

GC-MS (EI, 70 eV): m/z (%)=381 (M⁺, 85), 366 (M⁻-$CH_3$, 81), 336 (12), 295 (100), 252 (28), 224 (42), 193 (15), 165 (25), 135 (20), 91 (19), 59 (27).

L-I-1c $C_{26}H_{42}OSi_2$, $M_W$=426.77 g mol⁻¹

GC-MS (EI, 70 eV): m/z (%)=411 (M⁺-$CH_3$, 3), 369 (M⁺-$C_4H_9$, 100), 279 (9), 209 (32), 179 (7), 149 (42), 119 (11), 91 (100), 57 (5).

L-I-1f $C_{29}H_{49}NOSi_2$, $M_W$=483.89 g mol⁻¹

GC-MS (EI, 70 eV): m/z (%)=483 (M⁺, 5), 468 (M⁺-$CH_3$, 100), 426 (15), 369 (5), 267 (3), 193 (12), 147 (19), 91 (47), 58 (32).

Initiators used for producing polymer examples:

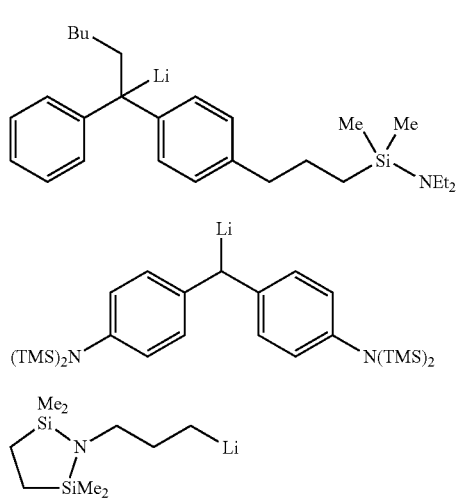

L1

L2

L3

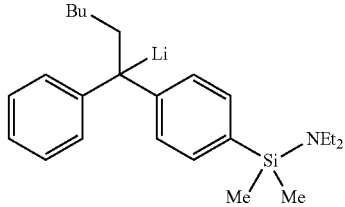

L4

L1 is an initiator according to Formula 2 of the present invention, prepared from the precursor compound according to Formula 1, whereas L2-L4 are prior art examples (see WO2014/040640, US2003/0114592, US2003/0114611, WO2000/050479, WO2000050478 and JP2012241112A).

II. Polymerization Procedures

Example A

Cyclohexane (4259.2 g), butadiene (625.7 g) and styrene (171.6 g) were charged to an airfree 10 l reactor and the stirred mixture was heated up to 40° C. Then TMEDA (0.24 g) was added and n-butyllithium was charged dropwise to react the impurities until the color of the reaction mixture changed to yellowish (titration). After that the recipe amount of L1 (4.01 mmol, c=0.193 mol/kg) in cyclohexane corresponding to the target molecular weight of the polymer was charged immediately to start the polymerization. The start time of the charge of the initiator was used as the start time of the polymerization. Parallel the temperature was increased by heating or cooling in the wall of the reactors beginning with the charge of the initiator to the final polymerization temperature of 60° C. for 80 min. Then butadiene (3.3 g) was charged followed by $SnCl_4$ (0.28 mmol) and 50 g cyclohexane via cylinder. The reaction was allowed to complete within 15 minutes followed by the last addition of butadiene (11.6 g). After 5 min chainend modifier 3-methoxy-3,8,8,9,9-pentamethyl-2-oxa-7-thia-3,8-disiladecane (5) (1.02 g) was added. The reaction was terminated after 20 min with charge of methanol (4.01 g). The polymer solution was stabilized with Irganox 1520D (2.03 g), the polymer recovered by steam stripping and dried until a content of residual volatiles <0.6% was obtained. The complete data set of the sample is given in table 1.

Reference Example B

Cyclohexane (3979.7 g), butadiene (579.5 g) and styrene (158.5 g) were charged to an airfree 10 l reactor and the stirred mixture was heated up to 40° C. Then TMEDA (0.22 g) was added and n-butyllithium was charged dropwise to react the impurities until the color of the reaction mixture changed to yellowish (titration). After that the recipe amount of L2 (5.29 mmol, c=0.201 mol/kg) in cyclohexane corresponding to the target molecular weight of the polymer was charged immediately to start the polymerization. The start time of the charge of the initiator was used as the start time of the polymerization. Parallel the temperature was increased by heating or cooling in the wall of the reactors beginning with the charge of the initiator to the final polymerization temperature of 60° C. for 80 min. Then butadiene (3.1 g) was charged followed by $SnCl_4$ (0.26 mmol) and 50 g cyclohexane via cylinder. The reaction was allowed to complete within 15 minutes followed by the last addition of butadiene (10.9 g). After 5 min chainend modifier 3-methoxy-3,8,8,9,9-pentamethyl-2-oxa-7-thia-3,8-disiladecane (5) (0.96 g) was added. The reaction was terminated after 20 min with charge of methanol (3.75 g). The polymer solution was stabilized with Irganox 1520D (1.90 g), the polymer recovered by steam stripping and dried until a content of residual volatiles <0.6% was obtained. The complete data set of the sample is given in table 1.

Reference Example C

Cyclohexane (4595 g), butadiene (675.3 g) and styrene (184.4 g) were charged to an airfree 10 l reactor and the stirred mixture was heated up to 40° C. Then TMEDA (1.01 g) was added and n-butyllithium was charged dropwise to react the impurities until the color of the reaction mixture changed to yellowish (titration). After that the recipe amount of L3 (4.33 mmol, c=0.191 mol/kg) in cyclohexane corresponding to the target molecular weight of the polymer was charged immediately to start the polymerization. The start time of the charge of the initiator was used as the start time of the polymerization. Parallel the temperature was increased by heating or cooling in the wall of the reactors beginning with the charge of the initiator to the final polymerization temperature of 60° C. for 80 min. Then butadiene (3.41 g) was charged followed by $SnCl_4$ (0.304 mmol) and 50 g cyclohexane via cylinder. The reaction was allowed to complete within 15 minutes followed by the last addition of butadiene (12.8 g). After 5 min chainend modifier 3-methoxy-3,8,8,9,9-pentamethyl-2-oxa-7-thia-3,8-disiladecane (5) (1.12 g) was added. The reaction was terminated after 20 min with charge of methanol (4.33 g). The polymer solution was stabilized with Irganox 1520D (2.19 g), the polymer recovered by steam stripping and dried until a content of residual volatiles <0.6% was obtained. The complete data set of the sample is given in table 1.

Reference Example D

Cyclohexane (2407 g), butadiene (301.5 g) and styrene (82.1 g) were charged to an airfree 5 l reactor and the stirred mixture was heated up to 40° C. Then TMEDA (0.1 g) was added and n-butyllithium was charged dropwise to react the impurities until the color of the reaction mixture changed to yellowish (titration). After that the recipe amount of L4 (1.64 mmol, c=0.084 mol/kg) in cyclohexane corresponding to the target molecular weight of the polymer was charged immediately to start the polymerization. The start time of the charge of the initiator was used as the start time of the polymerization. Parallel the temperature was increased by heating or cooling in the wall of the reactors beginning with the charge of the initiator to the final polymerization temperature of 60° C. for 80 min followed by the second addition of butadiene (7.8 g). After 5 min chain end modifier 3-methoxy-3,8,8,9,9-pentamethyl-2-oxa-7-thia-3,8-disiladecane (5) (0.62 g) was added. The reaction was terminated after 20 min with charge of methanol (0.05 g). The polymer solution was stabilized with Irganox 1520D (0.97 g), the polymer recovered by steam stripping and dried until a content of residual volatiles <0.6% was obtained. The complete data set of the sample is given in table 1.

Comparative Example 1

Cyclohexane (4653 g), butadiene (678.3 g) and styrene (185.3 g) were charged to an airfree 10 l reactor and the stirred mixture was heated up to 40° C. Then TMEDA (9.47 mmol) was added and n-butyllithium was charged dropwise to react the impurities until the color of the reaction mixture changed to yellowish (titration). After that the recipe amount of n-butyllithium (4.73 mmol) corresponding to the target molecular weight of the polymer was charged immediately via pump to start the polymerization. The start time of the charge of the main amount of n-butyllithium was used as the start time of the polymerization. Parallel the temperature was increased by heating or cooling in the wall of the reactors beginning with the charge of the main amount of n-butyllithium to the final polymerization temperature to of 60° C. for 80 min. Then butadiene (3.5 g) was charged followed by $SnCl_4$ (0.335 mmol) and 20 g cyclohexane via cylinder. The reaction was allowed to complete within 10 minutes followed by the last addition of butadiene (12.6 g). After 5 minutes chain end modifier 3-methoxy-3,8,8,9,9-pentamethyl-2-oxa-7-thia-3,8-disiladecane (5) (1.21 g) was added and the reaction mixture was stirred for a further 20 minutes. Then the reaction was terminated with charge of methanol (4.73 g). The polymer solution was stabilized with Irganox 1520D (2.2 g), the polymer recovered by steam stripping and dried until a content of residual volatiles <0.6% was obtained. The complete data set of the sample is given in table 1.

TABLE 1

Polymerisation details.

|  | Ex. A | Ref. Ex. B | Ref. Ex. C | Ref. Ex. D | Comp. Ex. 1 |
|---|---|---|---|---|---|
| Cyclohexane/g | 4529 | 3979.7 | 4595 | 2407 | 4653 |
| Butadiene/g | 640.6 | 593.5 | 691.5 | 309.3 | 694.5 |
| Styrene/g | 171.6 | 158.5 | 184.4 | 82.1 | 185.3 |
| TMEDA/mmol | 2.08 | 1.89 | 8.69 | 0.83 | 9.47 |
| Initiator/mmol | (L1) | (L2) | (L3) | (L4) | (nBuLi) |
|  | 4.01 | 5.29 | 4.33 | 1.64 | 4.73 |
| $SnCl_4$/mmol | 0.285 | 0.261 | 0.304 | — | 0.335 |
| Cpd 5/mmol | 3.624 | 3.248 | 3.80 | 2.10 | 4.16 |
| Mp/kg/mol | 296 | 302 | 303 | 325 | 294 |
| Vinyl content/% | 62.6 | 58.2 | 61.6 | 61.7 | 62.1 |
| Styrene content/% | 20.7 | 27.0 | 20.2 | 21.1 | 21.7 |
| $M_L$ | 62.8 | 38.7 | 52.9 | 58.1 | 55.0 |

Compounding in Silica:

TABLE 2

Compound information.

|  | Ex. A | Ref. Ex. B | Ref. Ex. C | Comp. Ex. 1 |
|---|---|---|---|---|
| ML1 + 4 100° C. unmassed | 62.1 | 41.6 | 56.8 | 53.4 |
| CML1 + 4 | 81.3 | 105.2 | 101.4 | 76.4 |
| CML-ML | 19.2 | 63.6 | 44.6 | 23.0 |
| Mod300-Mod100/MPa | 10.1 | 10.0 | 9.4 | 8.1 |
| Tensile strength/MPa | 17.3 | 17.9 | 19.9 | 19.4 |
| Rebound rt/% | 37.8 | 34.0 | 34.0 | 37.4 |
| Rebound 60° C./% | 63.4 | 60.8 | 57.0 | 59.4 |
| Hardness Shore A 0° C. | 64.3 | 64.9 | 71.3 | 64.7 |
| Hardness Shore A rt | 60.9 | 61.1 | 66.7 | 62.3 |
| Hardness Shore A 60° C. | 57.9 | 56.9 | 63.3 | 57.9 |
| HBU/° C. | 106.7 | 125.1 | 122.0 | 117.0 |
| Tan δ −10° C. | 0.522 | 0.584 | 0.463 | 0.463 |
| Tan δ 0° C. | 0.337 | 0.379 | 0.335 | 0.320 |
| Tan δ 60° C. | 0.090 | 0.104 | 0.117 | 0.123 |
| DIN abrasion [$mm^3$] | 126 | 132 | 143 | 129 |

Discussion:

Inventive Initiator (L1) is used to prepare inventive polymer A and compound A. Compound A exhibits the lowest CML-ML value of all compared compounds which corresponds to an excellent processing behavior. It also shows the highest polymer-filler interactions, as reflected by Mod300-Mod100. Outstanding hysteresis properties are illustrated by the lowest HBU and tan δ 60° C. as well as the highest Rebound at 60° C. in comparison to the other state of the art polymers with the same microstructure. Ice grip (tan δ−10° C.) and wet grip (tan δ 0° C.) are better than Comp. Ex. 1 and Ref. Ex. C. Only Ref. Ex B shows better ice grip and wet grip.

The wear characteristic of the inventive polymer is also very attractive.

Mixing Recipe

| 1st mixing stage: | |
| --- | --- |
| SSBR | 80 |
| High cis 1,4-polybutadiene (Buna™ cis 132-Schkopau, Styron Deutschland GmbH) | 20 |
| Precipitated silica (Silica 7000 GR, Evonik Industries) | 80 |
| Silane (Si 75, bis(triethoxysilylpropyl)disulfane, Evonik Industries) | 6.9 |
| Stearic acid (Cognis GmbH) | 1.0 |
| Antiozonant (Dusantox 6 PPD [N-(1,3-dimethylbutyl)-N'-phenyl-1,4-phenylenediamine], Duslo a.s.) | 2.0 |
| Zinc oxide (Grillo-Zinkoxid GmbH) | 2.5 |
| Ozone protecting wax (Antilux 654, Rhein Chemie Rheinau GmbH) | 1.5 |
| Softener (TDAE oil, VivaTec500, Hansen & Rosenthal KG) | 20 |
| 2nd mixing stage: | |
| Sulfur (Solvay AG) | 1.4 |
| Accelerator (TBBS, N-tert-butyl-2-benzothiazolesulfenamide, Rhein Chemie Rheinau GmbH) | 1.5 |
| DPG (diphenylguanidine, Vulkacit D, Lanxess AG) | 1.5 |

The invention claimed is:

1. A compound represented by the following Formula 1:

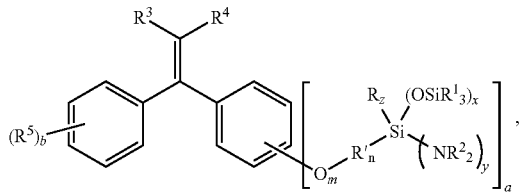

Formula I wherein
each R is independently selected from an optionally substituted organic group having from 1 to 12 carbon atoms, wherein R may be connected to one of the two benzene rings of Formula 1 to form a ring together with the Si atom of the aminosilyl group;
R' is an optionally substituted methylene group;
each $R^1$ is independently selected from an optionally substituted organic group having from 1 to 12 carbon atoms;
each $R^2$ is independently selected an optionally substituted organic group having from 1 to 12 carbon atoms, wherein the $R^2$ groups may be connected to each other to form a ring together with the Si-bonded nitrogen atom;
$R^3$ and $R^4$ are each independently selected from hydrogen, methyl, ethyl, propyl, butyl and vinyl;
each $R^5$ is independently selected from an optionally substituted hydrocarbon group having from 1 to 12 carbon atoms, a $C_1$-$C_6$ alkoxy group, a $C_1$-$C_6$ alkylthio group, and an amine group carrying two substituents independently selected from a $C_1$-$C_6$ alkyl group and a silyl group carrying three substituents independently selected from a $C_1$-$C_6$ alkyl group and a phenyl group;
a≥1; b≥0; a+b≤10;
m=0 or 1;
n=0 to 12;
x=0, 1 or 2; y=1, 2 or 3; z=0, 1 or 2; x+y+z=3; or x+y+z=2 when the silicon atom of the aminosilyl group is bonded twice to the benzene rings via groups R' or single bonds;
with the proviso that when m=1, then n=1 to 12, and when m=n=0, then x=1 or 2;
wherein the aminosilyl group(s) may be bonded to any of the two benzene rings, plural aminosilyl groups may be different from each other, and the $R^5$ group(s) may be bonded to any of the two benzene rings.

2. A polymerization initiator represented by the following Formula 2:

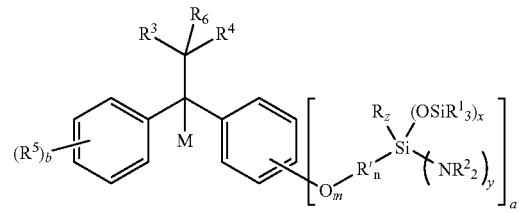

Formula 2 wherein
each R is independently selected from an optionally substituted organic group having from 1 to 12 carbon atoms, wherein R may be connected to one of the two benzene rings of Formula 1 to form a ring together with the Si atom of the aminosilyl group;
R' is an optionally substituted methylene group;
each $R^1$ is independently selected from an optionally substituted organic group having from 1 to 12 carbon atoms;
each $R^2$ is independently selected an optionally substituted organic group having from 1 to 12 carbon atoms, wherein the $R^2$ groups may be connected to each other to form a ring together with the Si-bonded nitrogen atom;
$R^3$ and $R^4$ are each independently selected from hydrogen, methyl, ethyl, propyl, butyl and vinyl;
each $R^5$ is independently selected from an optionally substituted hydrocarbon group having from 1 to 12 carbon atoms, a $C_1$-$C_6$ alkoxy group, a $C_1$-$C_6$ alkylthio group, and an amine group carrying two substituents independently selected from a $C_1$-$C_6$ alkyl group and a silyl group carrying three substituents independently selected from a $C_1$-$C_6$ alkyl group and a phenyl group;
$R^6$ is selected from $C_1$-$C_6$ alkyl, phenyl and benzyl;
M is an alkali metal selected from lithium, sodium and potassium;
a≥1; b≥0; a+b≤10;
m=0 or 1;
n=0 to 12;
x=0, 1 or 2; y=1, 2 or 3; z=0, 1 or 2; x+y+z=3; or x+y+z=2 when the silicon atom of the aminosilyl group is bonded twice to the benzene rings via groups R' or single bonds;

with the proviso that when m=1, then n=1 to 12, and when m=n=0, then x=1 or 2;

wherein the aminosilyl group(s) may be bonded to any of the two benzene rings, plural aminosilyl groups may be different from each other, and the $R^5$ group(s) may be bonded to any of the two benzene rings.

3. A method of making the polymerization initiator of Formula 2 as defined in claim 2, comprising the step of reacting (i) a compound of Formula 1

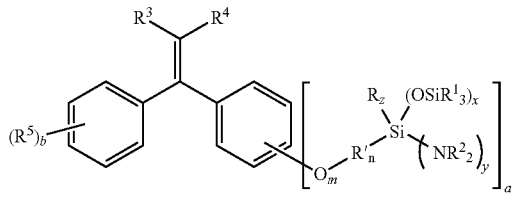

Formula I with (ii) at least one compound of the following Formula 3

$R^6M$    Formula 3 wherein Formula 1 is as defined in claim 1 and $R^6$ and M are as defined in claim 2.

4. The compound of claim 1, wherein each R is independently selected from a $C_1$-$C_{12}$ aliphatic group and a $C_3$-$C_{12}$ aromatic group, each of which may optionally be substituted.

5. The compound of claim 4, wherein the $C_1$-$C_{12}$ aliphatic group is linear, branched or cyclic and may be saturated or unsaturated.

6. The compound of claim 4, wherein the $C_3$-$C_{12}$ aromatic group is a homocyclic aromatic group or heterocyclic aromatic group.

7. The compound of claim 1, wherein each $R^1$ is independently selected from a $C_1$-$C_{12}$ aliphatic group and a $C_3$-$C_{12}$ aromatic group, each of which may optionally be substituted.

8. The compound of claim 7, wherein the $C_1$-$C_{12}$ aliphatic group is linear, branched or cyclic and may be saturated or unsaturated.

9. The compound of claim 7, wherein the $C_3$-$C_{12}$ aromatic group is a homocyclic aromatic group or heterocyclic aromatic group.

10. The compound of claim 1, wherein each $R^2$ is independently selected from a $C_1$-$C_{12}$ aliphatic group and a $C_3$-$C_{12}$ aromatic group, each of which may optionally be substituted and wherein the $R^2$ groups may be connected to each other to form a ring together with the Si-bonded nitrogen atom.

11. The compound of claim 10, wherein the $C_1$-$C_{12}$ aliphatic group is linear, branched or cyclic and may be saturated or unsaturated.

12. The compound of claim 10, wherein the $C_3$-$C_{12}$ aromatic group is a homocyclic aromatic group or heterocyclic aromatic group.

13. The compound of claim 1, wherein each $R^5$ is independently selected from a $C_1$-$C_{12}$ aliphatic group and a $C_3$-$C_{12}$ aromatic group, each of which may optionally be substituted.

14. The compound of claim 13, wherein the $C_1$-$C_{12}$ aliphatic group is linear, branched or cyclic and may be saturated or unsaturated.

15. The compound of claim 13, wherein the $C_3$-$C_{12}$ aromatic group is a homocyclic aromatic group or heterocyclic aromatic group.

16. The compound of claim 1, wherein the optional substituents are independently selected from a $C_1$-$C_{12}$ alkyl group, a $C_6$-$C_{12}$ aryl group, a $C_4$-$C_{12}$ heteroaryl group, $C_1$-$C_6$ alkoxy group, $C_1$-$C_6$ alkylthio group, a di($C_1$-$C_6$ alkyl)amino group, a diphenylamino group, a di($C_1$-$C_6$ alkyl)phosphino group, a diphenyl phosphine group, a $C_6$-$C_{12}$ aryloxy group, a $C_6$-$C_{12}$ arylthio group, a tri($C_1$-$C_6$ alkyl)silyl group, a tri($C_6$-$C_{12}$ aryl)silyl group and a tri (mixed $C_1$-$C_6$ alkyl and $C_6$-$C_{12}$ aryl)silyl group.

17. The compound of claim 1, wherein $R^3$ and $R^4$ are each independently selected from hydrogen, methyl and vinyl.

18. The polymerization initiator of claim 2, wherein $R^6$ is selected from methyl, n-butyl, sec-butyl, tert-butyl, benzyl and phenyl.

19. The polymerization initiator of claim 2, wherein M is lithium.

20. The polymerization initiator of claim 2, wherein each R is independently selected from $C_1$-$C_5$ alkyl and $C_6$ aryl, each $R^1$ is independently selected from $C_1$-$C_4$ alkyl and $C_6$ aryl, each $R^2$ is independently selected from $C_1$-$C_8$ alkyl and $C_7$-$C_{10}$ alkylaryl, $R^3$ and $R^4$ are each hydrogen, each $R^5$ is independently selected from $C_1$-$C_4$ alkyl, $R^6$ is selected from methyl, ethyl, tert-butyl, n-butyl, sec-butyl, phenyl and benzyl, M is lithium, a=1 or 2, b=0 or 1, m=0 and R' is methylene and n=1, 2 or 3, x=0 or 1, y=1 or 2 and z=0 or 1.

21. A polymer which is the reaction product of
   i) a polymerization initiator of Formula 2 as defined in claim 2 and
   ii) one or more polymerizable monomers selected from conjugated dienes and optionally one or more polymerizable monomers selected from aromatic vinyl compounds, or
   i') a polymerization initiator other than that of Formula 2 as defined in claim 2,
   ii') one or more polymerizable monomers selected from conjugated dienes and optionally one or more polymerizable monomers selected from aromatic vinyl compounds, and
   iii') a compound of Formula 1 as defined in claim 1 which is used as backbone-modifying agent and/or chain end-modifying agent.

22. A method of making a polymer, comprising the step of reacting
   i) a polymerization initiator of Formula 2 as defined in claim 2 and
   ii) one or more polymerizable monomers selected from conjugated dienes and optionally one or more polymerizable monomers selected from aromatic vinyl compounds, or
   i') a polymerization initiator other than that of Formula 2 as defined in claim 2,
   ii') one or more polymerizable monomers selected from conjugated dienes and optionally one or more polymerizable monomers selected from aromatic vinyl compounds, and
   iii') a compound of Formula 1 as defined in claim 1 which is used as backbone-modifying agent and/or chain end-modifying agent.

23. A polymer composition comprising the polymer as defined in claim 21 and one or more further components selected from (i) components which are added to or formed as a result of the polymerization process used for making said polymer and (ii) components which remain after solvent removal from the polymerization process.

24. The polymer composition according to claim 23 further comprising one or more extender oils.

25. The polymer composition according to claim 23, further comprising one or more fillers.

26. The polymer composition according to claim 23, further comprising at least one vulcanizing agent.

27. A vulcanized polymer composition which is obtained by vulcanizing the polymer composition as defined in claim 26.

28. A method of making a vulcanized polymer composition, comprising the step of vulcanizing the polymer composition as defined in claim 26.

29. An article comprising at least one component formed from the vulcanized polymer composition as defined in claim 27.

* * * * *